(12) United States Patent
Guccione et al.

(10) Patent No.: US 12,188,016 B2
(45) Date of Patent: Jan. 7, 2025

(54) ANTISENSE OLIGONUCLEOTIDES FOR MODULATING THE FUNCTION OF A T CELL

(71) Applicants: AGENCY FOR SCIENCE, TECHNOLOGY AND RESEARCH, Singapore (SG); LION TCR PTE. LTD., Singapore (SG)

(72) Inventors: Ernest Guccione, Singapore (SG); Dave Keng Boon Wee, Singapore (SG); Antonio Bertoletti, Singapore (SG)

(73) Assignees: AGENCY FOR SCIENCE, TECHNOLOGY AND RESEARCH, Singapore (SG); LION TCR PTE. LTD., Singapore (SG)

( * ) Notice: Subject to any disclaimer, the term of this patent is extended or adjusted under 35 U.S.C. 154(b) by 643 days.

(21) Appl. No.: 16/626,395

(22) PCT Filed: Jun. 27, 2018

(86) PCT No.: PCT/SG2018/050313
§ 371 (c)(1),
(2) Date: Dec. 24, 2019

(87) PCT Pub. No.: WO2019/004939
PCT Pub. Date: Jan. 3, 2019

(65) Prior Publication Data
US 2020/0377883 A1 Dec. 3, 2020

(30) Foreign Application Priority Data
Jun. 27, 2017 (SG) .............................. 10201705285S

(51) Int. Cl.
*C12N 15/11* (2006.01)
*A61K 31/7088* (2006.01)
*A61K 35/17* (2015.01)
*A61P 35/00* (2006.01)
*C12N 15/113* (2010.01)

(52) U.S. Cl.
CPC ........ *C12N 15/113* (2013.01); *A61K 31/7088* (2013.01); *A61K 35/17* (2013.01); *A61P 35/00* (2018.01); *C12N 15/1136* (2013.01); *C12N 15/1138* (2013.01); *C12N 2310/11* (2013.01); *C12N 2310/351* (2013.01); *C12N 2320/33* (2013.01)

(58) Field of Classification Search
CPC .............. C12N 15/113; C12N 2310/11; C12N 2320/33
See application file for complete search history.

(56) References Cited

FOREIGN PATENT DOCUMENTS

| | | | |
|---|---|---|---|
| CN | 103820454 | 5/2014 | |
| EP | 2735568 | 5/2014 | |
| WO | 02/088162 A1 | 11/2002 | |
| WO | 2007056466 | 5/2007 | |
| WO | 2010054267 | 5/2010 | |
| WO | WO-2011029914 A1 * | 3/2011 | ......... C12N 15/1137 |
| WO | 2011120101 | 10/2011 | |
| WO | 2013135830 | 9/2013 | |
| WO | 2014078749 | 5/2014 | |
| WO | 2014/090985 A1 | 6/2014 | |
| WO | 2014184741 | 11/2014 | |
| WO | 2015161276 | 10/2015 | |
| WO | WO-2015161276 A2 * | 10/2015 | ............. A61K 48/00 |
| WO | 2016/138278 A2 | 9/2016 | |
| WO | 2016160721 | 10/2016 | |
| WO | 2016/196388 A1 | 12/2016 | |
| WO | 2017093969 | 6/2017 | |

OTHER PUBLICATIONS

NCBI Reference Sequence NM_005018.3, GenBank, 1997, pp. 1-5 (Year: 1997).*
Sequence listing from WO 2015161276, pp. 1-839 (Year: 2015).*
International Preliminary Report on Patentability issued in PCT/SG2018/050313, dated Sep. 3, 2019, 25 pages.
Bochan, Markian R., W. Scott Goebel, and Zacharie Brahmi. "Stably transfected antisense granzyme B and perforin constructs inhibit human granule-mediated lytic ability." Cellular immunology 164.2 (1995): 234-239.
Acha-Orbea, Hans, et al. "Inhibition of lymphocyte mediated cytotoxicity by perforin antisense oligonucleotides." The EMBO journal 9.12 (1990): 3815-3819.
Spaner, David, et al. "A role for perforin in activation-induced cell death." The Journal of Immunology 160.6 (1998): 2655-2664.
Bertoletti, Antonio, et al. "T cell receptor-therapy in HBV-related hepatocellularcarcinoma." Oncoimmunology 4.6 (2015): e1008354, 1-3. Mar. 19, 2015.
Roth, Evelyn, and Hanspeter Pircher. "IFN-γ promotes Fas ligand- and perforin-mediated liver cell destruction by cytotoxic CD8 T cells." The Journal of Immunology 172.3 (2004): 1588-1594.
Sharpe, Michaela, and Natalie Mount. "Genetically modified T cells in cancer therapy: opportunities and challenges." Disease models & mechanisms 8.4 (2015): 337-350.
Pardee, Angela D., and Lisa H. Butterfield. "Immunotherapy of hepatocellular carcinoma: unique challenges and clinical opportunities." Oncoimmunology 1.1 (2012): 48-55.

(Continued)

*Primary Examiner* — Ekaterina Poliakova-Georgantas
(74) *Attorney, Agent, or Firm* — Meunier Carlin & Curfman LLC

(57) ABSTRACT

The present invention relates to antisense oligonucleotides for modulating the function of a T cell, including antisense oligonucleotides that hybridise to IFN-γ, granzyme, perforin 1, PD-1, PRDM1, PD-L1, CD40LG, NDFIP1, PDCD1 LG2, REL, BTLA, CD80, CD160, CD244, LAG3, TIGIT, ADORA2A & TIM-3 RNAs. In particular, the present invention relates to antisense oligonucleotides capable of inducing exon skipping of RNA. Also claimed is a method for further modifying the specificity of said T-cell by providing for a T cell receptor gene.

Figure 1:
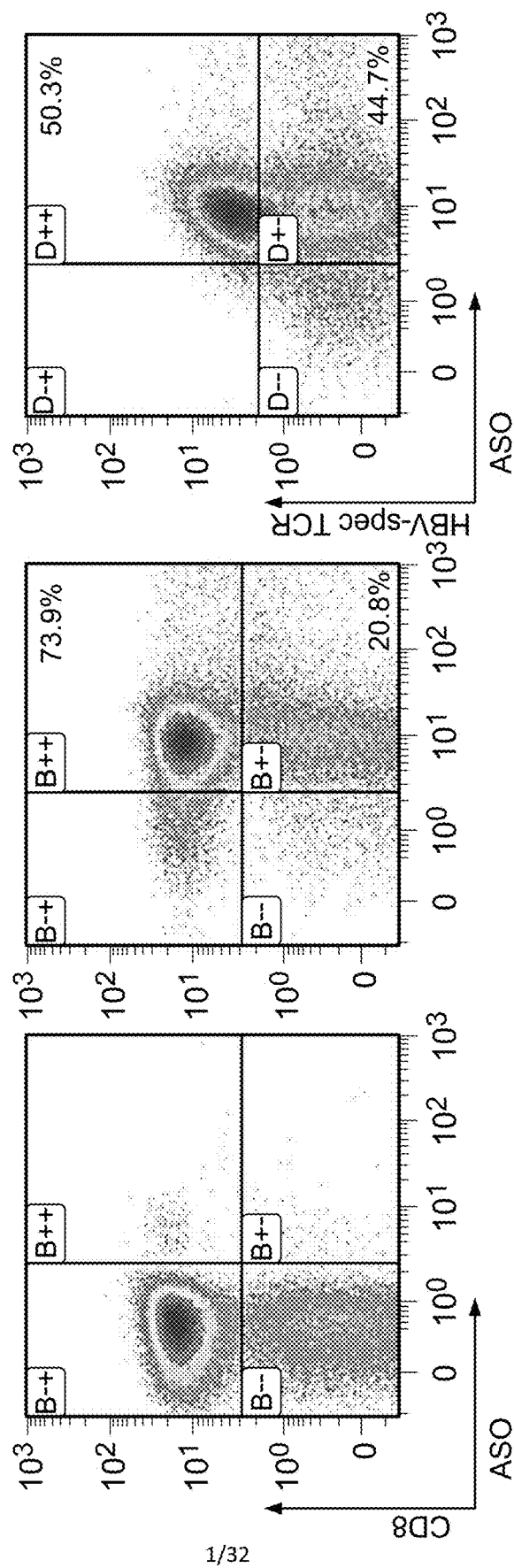

24 Claims, 32 Drawing Sheets
Specification includes a Sequence Listing.

(56) References Cited

OTHER PUBLICATIONS

Kudo, Masatoshi. "Immune checkpoint inhibition in hepatocellular carcinoma: basics and ongoing clinical trials." Oncology 92.Suppl. 1 (2017): 50-62.
International Search Report and Written Opinion issued by the International Searching Authority (ISA/SG) in PCT Application No. PCT/SG2018/050313 on Sep. 14, 2018. 19 pages.
Australian Examination Report issued for Application No. 2018291556, dated Nov. 17, 2020.
Australian Examination Report issued for Application No. 2018291556, dated Nov. 8, 2021.
European Extended Search Report issued for Application No. 18823314.2, dated Jun. 21, 2021.
Śledzińska, Anna, et al. "Negative immune checkpoints on T lymphocytes and their relevance to cancer immunotherapy." Molecular oncology 9.10 (2015): 1936-1965.
Cao, Yang, et al. "Tim-3 expression in cervical cancer promotes tumor metastasis." PloS one 8.1 (2013): e53834.
Beavis, Paul A., et al. "Targeting the adenosine 2A receptor enhances chimeric antigen receptor T cell efficacy." The Journal of clinical investigation 127.3 (2017): 929-941.
Andrews, Lawrence P., et al. "LAG 3 (CD 223) as a cancer immunotherapy target." Immunological reviews 276.1 (2017): 80-96.
Jennifer Couzin-Frankel, "Cancer Immunotherapy," Science vol. 342, No. 6165, December, p. 1432-3, 2013.
K. C. M. Straathof, C. M. Bollard, U. Popat, M. H. Huls, T. Lopez, M. C. Morriss, M. V Gresik, A. P. Gee, H. V Russell, M. K. Brenner, C. M. Rooney, and H. E. Heslop, "Treatment of nasopharyngeal carcinoma with Epstein-Barr virus-specific T lymphocytes," Therapy, vol. 105, No. 5, pp. 1898-1904, 2005.
M. H. Geukes Foppen, M. Donia, I. M. Svane, and J. B. a G. Haanen, "Tumor-infiltrating lymphocytes for the treatment of metastatic cancer," Mol. Oncol., vol. 9, No. 10, pp. 1918-1935, 2015.
W. Qasim and A. J. Thrasher, "Progress and prospects for engineered T cell therapies," Br. J. Haematol., vol. 166, No. 6, pp. 818-829, 2014.
B. Savoldo, C. A. Ramos, E. Liu, M. P. Mims, M. J. Keating, G. Carrum, R. T. Kamble, C. M. Bollard, A. P. Gee, Z. Mei, H. Liu, B. Grilley, C. M. Rooney, H. E. Heslop, M. K. Brenner, and G. Dotti, "CD28 costimulation improves expansion and persistence of chimeric antigen receptor-modified T cells in lymphoma patients," . Clin. Invest., vol. 121, No. 5, pp. 1822-1826, 2011.
L. A. Johnson, R. a Morgan, M. E. Dudley, L. Cassard, J. C. Yang, M. S, U. S. Kammula, R. E. Royal, R. M. Sherry, J. R. Wunderlich, and C. R. Lee, "regression and targets normal tissues expressing cognate antigen Gene therapy with human and mouse T cell receptors mediates cancer regression and targets normal tissues expressing cognate antigen," Hematology, vol. 114, No. 3, pp. 535-547, 2009.
A. J. Gehring, S. A. Xue, Z. Z. Ho, D. Teoh, C. Ruedl, A. Chia, S. Koh, S. G. Lim, M. K. Maini, H. Stauss, and A. Bertoletti, "Engineering virus-specific T cells that target HBV infected hepatocytes and hepatocellular carcinoma cell lines," Hepatol., vol. 55, No. 1, pp. 103-110, 2011.
W. Qasim, M. Brunetto, A. J. Gehring, S.-A. Xue, A. Schurich, A. Khakpoor, H. Zhan, P. Ciccorossi, K. Gilmour, D. Cavallone, F. Moriconi, F. Farzhenah, A. Mazzoni, L. Chan, E. Morris, A. Thrasher, M. K. Maini, F. Bonino, H. Stauss, and A. Bertoletti, "Immunotherapy of HCC metastases with autologous T cell receptor redirected T cells, targeting HBsAg in a liver transplant patient.," J. Hepatol., vol. 62, No. 2, pp. 486-491, 2015.
S. Koh, N. Shimasaki, R. Suwanarusk, Z. Z. Ho, A. Chia, N. Banu, S. W. Howland, A. S. M. Ong, A. J. Gehring, H. Stauss, L. Renia, M. Sallberg, D. Campana, and A. Bertoletti, "A practical approach to immunotherapy of hepatocellular carcinoma using T cells redirected against hepatitis B virus.," Mol. Ther. Nucleic Acids, vol. 2, No. August, p. el 14, 2013.
E. J. Wherry, S. J. Ha, S. M. Kaech, W. N. Haining, S. Sarkar, V. Kalia, S. Subramaniam, J. N. Blattman, D. L. Barber, and R. Ahmed, "Molecular Signature of CD8+ T Cell Exhaustion during Chronic Viral Infection," Immunity, vol. 27, No. 4, pp. 670-684, 2007.
P. A. Morcos, "Achieving targeted and quantifiable alteration of mRNA splicing with Morpholino oligos," Biochem. Biophys. Res. Commun., vol. 358, No. 2, pp. 521-527, 2007.
G. Schmajuk, H. Sierakowska, and R. Kole, "Antisense Oligonucleotides with Different Backbones," J. Biol. Chem., vol. 274, No. 31, pp. 21783-21789, 1999.
E. M. McNally and E. J. Wyatt, "Welcome to the splice age: Antisense oligonucleotide-mediated exon skipping gains wider applicability," . Clin. Invest., vol. 126, No. 4, pp. 1236-1238, 2016.
A Phase I/IIa Clinical Trial in Duchenne Muscular Dystrophy Using Systemically Delivered Morpholino Antisense Oligomer to Skip Exon 53 (SKIP-NMD). (2015). Human Gene Therapy Clinical Development, 26(2), 92-95. doi:10.1089/humc.2015.2528.
Goemans, N. M., Tulinius, M., van den Akker, J. T., Burm, B. E., Ekhart, P. F., Heuvelmans, N., . . . van Deutekom, J. C. (2011). Systemic Administration of PRO051 in Duchenne's Muscular Dystrophy. New England Journal of Medicine, 364(16), 1513-1522. doi:10.1056/nejmoa1011367.
N. J. Gogtay and K. Sridharan, "Therapeutic Nucleic Acids: Current clinical status.," Br. J. Clin. Pharmacol., pp. 1-14, 2016.
J. Jo, U. Aichele, N. Kersting, R. Klein, P. Aichele, E. Bisse, A. K. Sewell, H. E. Blum, R. Bartenschlager, V. Lohmann, and R. Thimme, "Analysis of CD8+ T-Cell-Mediated Inhibition of Hepatitis C Virus Replication Using a Novel Immunological Model," Gastroenterology, vol. 136, No. 4, pp. 1391-1401, 2009.
A. J. Davenport, M. R. Jenkins, R. S. Cross, C. S. Yong, H. M. Prince, D. S. Ritchie, J. a Trapani, M. H. Kershaw, P.K. Darcy, and P.J. Neeson, "CAR-T Cells Inflict Sequential Killing of Multiple Tumor Target Cells.," Cancer Immunol. Res., vol. 3, No. 5, pp. 483-494, 2015.

* cited by examiner

A

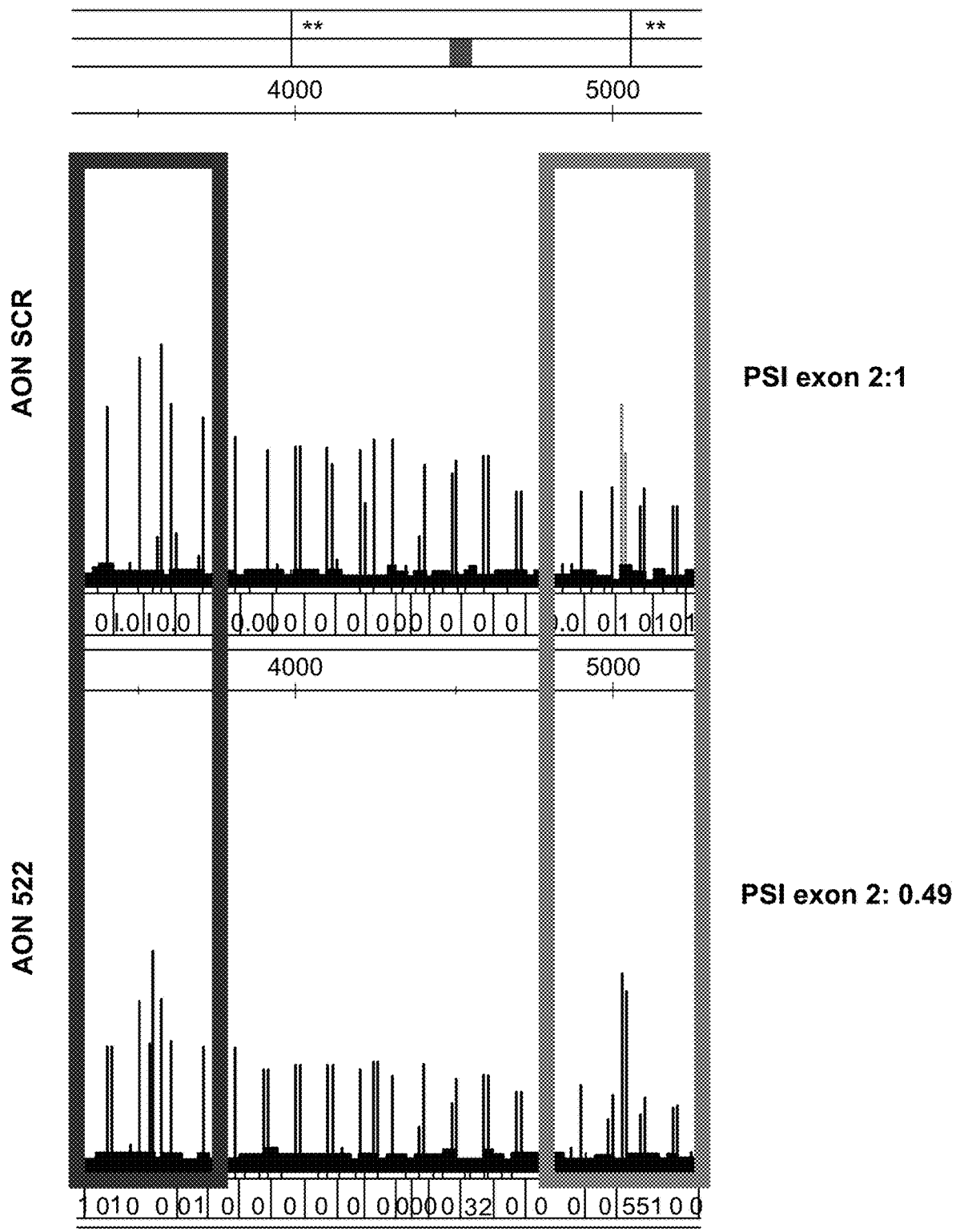

| | | |
|---|---|---|
| 0218_1173_2OM_E3 | CTLA4 | 5' - mG*mG*mA*mA*mG*mU*mC*mA*mA*mG*mA*mU*mG*mG*mG*mC*mA*mC*mA*mG*mG*mG*mU - 3' |
| 0218_1174_2OM_E3 | CTLA4 | 5' - mU*mA*mA*mC*mC*mU*mG*mC*mG*mU*mG*mC*mC*mC*mA*mU*mG*mG*mA*mG*mA*mG*mG - 3' |
| 1117_930_2OM_E2 | ADORA2A | 5' - mG*mG*mC*mG*mC*mG*mU*mC*mU*mG*mG*mC*mC*mU*mU*mU*mU*mC - 3' |
| 1117_931_2OM_E2 | ADORA2A | 5' - mG*mC*mA*mU*mC*mA*mC*mC*mA*mG*mG*mC*mA*mG*mG*mG*mC*mA*mG*mG*mG*mU - 3' |
| 0817_887_2OM_E3 | PD-1 | 5' - mG*mA*mC*mA*mC*mC*mA*mC*mC*mA*mG*mG*mU*mU*mU*mG*mG - 3' |
| 0817_888_2OM_E3 | PD-1 | 5' - mC*mG*mG*mC*mC*mG*mG*mA*mG*mU*mG*mG*mG*mG - 3' |
| 0817_889_2OM_E4 | PD-1 | 5' - mA*mU*mG*mG*mU*mC*mU*mC*mA*mA*mA*mC*mA*mC*mA*mC*mC*mA*mU*mU*mG*mG - 3' |
| 0817_890_2OM_E4 | PD-1 | 5' - mA*mC*mU*mG*mA*mC*mU*mC*mA*mG*mG*mG*mG*mG*mC*mU*mG - 3' |

Figure 24

ANTISENSE OLIGONUCLEOTIDES FOR MODULATING THE FUNCTION OF A T CELL

REFERENCE TO SEQUENCE LISTING

The Sequence Listing submitted Aug. 5, 2020, as a text file named "007593981_final_ST25.txt" created on Aug. 5, 2020, and having a size of 15.9 MB is hereby incorporated by reference pursuant to 37 C.F.R. § 1.52 (e) (5).

The present invention relates to antisense oligonucleotides. In particular, the present invention relates to antisense oligonucleotides capable of inducing exon skipping. More particularly, the present invention relates to the use of such antisense oligonucleotides in the field of immunotherapy, specifically to that of immunotherapy directed against tumours and/or viral infections (such as Hepatitis B induced Hepatocellular Carcinoma, EBV induced NKT cell Lymphmas and other chronic infections such as chronic HBV infection and human cytomegalovirus infection etc.).

It is here shown that direct and selective downregulation of immune-related or immunomodulatory genes expressed by T cells (e.g. by Antisense OligoNucleotide (ASO)-mediated exon skipping or intron retention), leads to modulation of T cell functions (such as increased expansion, ability to kill or production of antiviral cytokines).

Cancer immunotherapy has been declared "Breakthrough of the year 2013" by the journal Science [1]. The statement made by the editors is justified by several promising clinical trials that are currently ongoing and by the wish to acknowledge a new paradigm shift: the therapy is now directed towards the immune system, rather than against the tumor [2]. The change of strategy is supported by failures from various other approaches and by new findings that lead to define 'immune evasion" as a novel hallmark of cancer. In fact, new progresses in the field have demonstrated that the immune system is actively playing a role in surveillance and tumor eradication, as cancer cells often have modified molecules on their surface that can be potentially detected (tumor-associated antigens), leading to their elimination. Nonetheless, cancer often is able to evade the inspection or silence the immune response. Thus, the restoration of a functional and prompt immune anti-tumoral activity could serve as an improvement in the long-unresolved battle against cancer.

One of the first approaches of immunotherapy consisted in the administration of cytokines (e.g. IL-2) able to stimulate the immune system, while nowadays both adoptive T-cell transfer and immune checkpoint blockade are widely used [3]. Adoptive T-cell transfer is the administration of engineered lymphocytes into a patient and the engineering process aims at T-cell activation and/or redirection against the tumor-associated antigens. Various proof-of-concept studies have already revealed the potential of engineered T-cells in adoptive transfer therapy and the key idea is the redirection of T-cell specificity through the transfer of antigen receptor genes. Few strategies have been developed in the past couple of decades and they involve recombinant variants of conventional T-cell receptors (TCRs), or composites of antibody-like receptor chains linked to transmembrane and activation domains (CARs) [4].

Chimeric antigen receptors (CARs) are made of three functional units: an extracellular domain for the antigen recognition, a transmembrane anchor and an intracellular signalling domain [5]. The first is an antibody-like single chain, whose main advantages are the strength in the antigen binding (many fold higher than conventional T-cell receptors) and the fact that the recognition is not HLA-restricted or dependent on antigen presentation pathways on antigen presenting cells (APCs). The signalling domain is instead derived from elements of CD3f in combination with a costimulatory domain. CARs have evolved significantly over the past few decades and many studies are ongoing and giving encouraging results; however at present only few specific targets have been identified and, moreover, these receptors might be immunogenic, due to their non-physiological nature.

The T-cell receptors (TCR) used for adoptive immune therapy are constituted by physiological αβ heterodimers engineered to avoid the dimerization with the endogenous TCR chains and they are expressed with signalling elements of the CD3 complex [6]. TCRs bind to antigens presented on their surface in combination with a MHC-I (Major Histocompatibility Complex-I) molecule. This approach is limited to settings where TCR against a MHC-I/peptide complex have already been isolated and characterized from antigen-specific T-cells, and it relies on the presentation pathways of cancer cells. However, in contrast to CARs, TCRs possess physiological structures that are non-immunogenic and their activity in vivo is already known in physiological conditions.

In the context of chronic Hepatitis B or Hepatitis B virus (HBV)-related hepatocellular carcinoma (HCC), adoptive T-cell therapy has shown positive results. In particular, T-cells transduced with a viral vector expressing a HLA-restricted HBV-specific TCR are able to recognize peptides derived from the core and the envelope proteins of the virus presented in association with a MHC-I molecule [7]. The recognition induces an activation of the HBV-specific T-cells that results in the lysis of HBV infected cells. Moreover, the same cells were successfully used in a patient with HBsAg positive HCC relapses [8]. The HBV-specific TCR-redirected T-cells infused in the patient were able to proliferate in vivo, and in vitro tests confirmed their specificity and their activation status. The immunotherapy induced a drop of HBsAg levels after 4 weeks of treatment together with an increase in T-cell chemokines and ALT (alanine transaminase, a marker of hepatocyte lysis).

However, the use in therapy of stably retro or lentiviral-transduced cells may raise concerns from two different points of view: first of all, the risk of insertional mutagenesis can never be totally excluded; second, the presence of high quantities of HBV-targeting T-cells can lead to hepatotoxicity, as up to 90% of the liver of chronic patients could be infected by the virus. Various strategies are being investigated, and one of them is the transfection of the mRNA coding for the HBV-specific TCR via electroporation; this method eliminates the use of the lentiviral system and, moreover, it leads to a transient expression of the TCR. T-cells electroporated with a mRNA coding the α/β chains of a HBV-specific TCR can express the T-cell receptor at higher frequency compared to those transfected with a retro- or lentiviral system [9]. These electroporated cells were able to lyse the antigen-expressing targets in vitro, and to block tumor growth in a mouse PDX model. The advantages of this method are the high transfection rate and transient expression of the TCR. The last point might be seen as a disadvantage, requiring multiple infusions of the transfected T-cells to the patient, but safety-wise the improvement is significant, since the HBV specificity will be lost after a few days, limiting liver damage.

Given the possibility to modify the specificity of T-cell, we asked whether it would be possible to additionally modify their function. For example, it could be beneficial to enhance the ability of T-cells to fight cancer cells by blocking the immune checkpoint molecules that lead T-cells to be deleted or exhausted in the tumor microenvironment, such as PD-1 and CTLA-4 [10]. Alternatively it could be important to have T cells that have a reduced killing capacity, limiting their potential toxic side effects (e.g. by downregulating the levels of Perforin or Granzyme). Among the different strategies commonly used to modify cellular expression (CRISPR/Cas9-mediated, TALEN-mediated, RNA-interference), we chose to use the antisense technology via the AntiSense Oligonucleotides (ASOs) [11]. The ASOs are short oligomers (about 25/30 bases long) of chemically modified RNA that are able to anneal to the pre-mRNA of the target genes and interfere with their physiological splicings [12]. ASOs need to be chemically modified to improve their resistance to nucleases and provide favourable pharmacokinetic and pharmacodynamic properties for in vivo use. ASOs are designed to anneal to the pre-mRNA at specific sites in order to mask the cis-elements required for a correct splicing, therefore altering the interaction between the target pre-mRNA and the splicing machinery. As a consequence, this will lead to substantial defects in the processed mRNA that will eventually affect its stability and translation. This mechanism can be exploited to obtain knockdown of the function of an undesired gene, by inducing the exclusion from the mature mRNA of an exon that is fundamental for the function or the stability of the protein. The elimination could in fact lead to the creation of mRNA isoforms that encode non-functional proteins or trigger nonsense-mediated decay (NMD) of the mRNA [13].

In the past few years, antisense-mediated splicing modulation has advanced steadily and has been developed from preclinical models into the clinical trial phase for Duchenne muscular dystrophy and spinal muscular atrophy, showing remarkable results, preparing the ground for more exciting advances in genetic therapy [14] [15]. Other methods, such as RNA interference or translation inhibition, could be used if simple knockdown is desired, but it has been demonstrated that ASOs have less off-target effects and higher in vivo stability, making them more suitable and appealing for clinical development [16].

Antisense oligonucleotides (ASOs) that interfere with the splicing of granzyme B and perforin pre-mRNAs were designed and introduced in human lymphocytes in combination with mRNA coding for the V alpha/beta chains of HBV-specific T-cells. The efficiency of ASOs to modify the cytotoxic T-cell function of TCR-redirected T-cells was analysed. We demonstrated that 24 hours after the electroporation 50% of the lymphocytes express the HBV-specific TCR and show significant alteration of the ASO-targeted mRNAs. At the protein level, HBV-specific TCR-redirected T-cells showed a reduction of 40% in perforin expression. Consequently, the knock down of perforin lead to a decrease of 35% in the T-cell ability to lyse HBV-infected targets. However, no impairment of the antiviral activity was detected together with the decrease in cytotoxicity.

In conclusion, we demonstrated that we are able to transiently redirect the antigen specificity of T-cells for recognition of specific viral antigens and simultaneously modulate their function. After having proven the efficiency of the method with few proof-of-concept experiments, we aim to modify TCR-redirected T-cells in order to increase their efficacy in tumor microenvironments. In summary, our results look promising for the design of more efficient effectors that could be more safely applied in targeted and personalized treatments of tumors and chronic viral infections.

The present invention provides direct and selective modulators of T cell functions. With direct, it is meant that we will directly modulate the expression or splicing of key genes involved in T cell functionality. With selective, it is meant that the modulation is sequence specific and does not modulate the expression or splicing of other mRNAs. This is important to prevent unwanted side effects (i.e. iatrogenic effects caused by the therapy), given that aberrant modulation of splicing might be associated with pathologies (e.g. cancer). This is equivalent as saying that methods of treating cancer in a subject are provided, comprising a step of administering TCR-redirected T cells modified ex vivo in their functions (e.g. ability to kill target cells, or to inhibit viral replication). Such modification of functions may be achieved by administering ex vivo Antisense Oligonucleotides to T cells.

According to particular embodiments, the cancer expresses a specific antigen, which can be targeted by TCR-redirected T cells (e.g. a viral HBV protein). According to particular embodiments expression of a specific antigen means it can be detected by sequencing methods. According to particular embodiments, the cancer is selected from the group of virally induced or expressing cancers (e.g. HBV induced HCC, EBV induced NKT Lymphoma). Although any direct and selective modulator of T cell functions can be suitable for the methods taught herein (e.g. small molecules, lentiviral- or retroviral based shRNA or CRISPR vectors) it is particularly envisaged that the T cell modulator acts at the RNA level. More specifically, the inhibitor is an antisense oligonucleotide (ASO). The antisense oligonucleotides should affect the expression or splicing of genes important for T cell functions (e.g. IFNgamma, Perforin, Granzyme, PD-1). Even more particularly envisaged is an antisense oligonucleotide that induces exon skipping. Most particularly, the exon that is skipped is either exon 2 or 3 for IFNgamma, exon 2b for Perforin, exon 3 for Granzyme, exon 2 for PD-1 Accordingly, also provided herein are antisense oligonucleotides that induce exon skipping in the afore mentioned transcripts. Such antisense oligonucleotides are also provided for use as a medicament. Particularly, they are provided for cancer immunotherapy. The ASOs may be used as a single agents, or simultaneously electroporated into T-cells to modify their functions.

The listing or discussion of an apparently prior-published document in this specification should not necessarily be taken as an acknowledgement that the document is part of the state of the art or is common general knowledge.

Any document referred to herein is hereby incorporated by reference in its entirety.

The disclosure is directed to one or more antisense polynucleotides and their use in pharmaceutical compositions in a strategy against tumors and/or viral infections (such as Hepatitis B induced Hepatocellular Carcinoma, EBV induced NKT cell Lymphmas etc.). It is here shown that direct and selective downregulation of immune-related or immunomodulatory genes expressed by T cells (e.g. by Antisense OligoNucleotide (ASO)-mediated exon skipping or intron retention), leads to modulation of T cell functions (such as direct inhibition of viral replication or selective killing of cells expressing a targeted antigen).

In a first aspect of the present invention, there is provided an antisense oligonucleotide that modulates the function of a T-cell.

By the term "modulating the function", it is meant to include any inhibition or an increase of the activity of . . . includes inhibition, decrease, regulation or enhancing of a function of a T cell, e.g. a T cell's response in a human, a T cell's interaction with a target etc. In various embodiments, the antisense oligonucleotide modulates one or more of T-cell expansion, T-cell ability to kill or produce an anti-viral cytokines.

The activity of a T cell may be measured using any suitable in vitro, cellular or in vivo assay, by at least 1%, preferably at least 5%, such as at least 10% or at least 25%, for example by at least 50%, at least 60%, at least 70%, at least 80%, or 90% or more, compared to activity of T cell that is not transfection by an ASO of the present invention, in the same assay under the same conditions but without the presence of the an ASO sequence. As will be clear to the skilled person, "modulating" may also involve effecting a change (which may either be an increase or a decrease) in affinity, avidity, specificity and/or selectivity of the T-cell receptor, for one or more of its targets, ligands, receptors or substrates. As will be clear to the skilled person, this may again be determined in any suitable manner and/or using any suitable assay known per se, such as the assays described herein or in the prior art cited herein.

"Modulating" may also mean effecting a change (i.e. an activity as an agonist or as an antagonist, respectively) with respect to one or more biological or physiological mechanisms, effects, responses, functions, pathways or activities in which the T-cell receptor and their targets are involved, such as its signaling pathway or metabolic pathway and their associated biological or physiological effects. Again, as will be clear to the skilled person, such an action as an agonist or an antagonist may be determined in any suitable manner and/or using any suitable (in vitro and usually cellular or in assay) assay known per se. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of an ASO of the invention.

In some embodiments, the antisense oligonucleotide modulates one or more of activity, or level of expression of an immune-related or immunomodulatory genes expressed by the T-cell, with the proviso that the gene is not a CTLA4 gene. The level of expression includes modulation of splicing to alter isoform expression of the immune-related or immunomodulatory gene.

In other embodiments, the antisense oligonucleotide modulates the function of the T cell by blocking an immune checkpoint molecule. The immune checkpoint molecule may be PD-1.

In other embodiments, the level of expression is one of directly or selectively downregulating the immune-related or immunomodulatory gene. The oligonucleotide specifically hybridises to a target region of the immune-related or immunomodulatory gene's pre-mRNA or mature mRNA, the gene may be any one selected from the group comprising: IFN-γ, Granzyme, Perforin1, PD-1, PRDM1, PD-L1, CD40LG, NDFIP1, PDCD1LG2, REL, BTLA, CD80, CD160, CD244, LAG3, TIGIT and TIM-3.

By "hybridisation" means an interaction between two or three strands of nucleic acids by hydrogen bonds in accordance with the rules of Watson-Crick DNA complementarity, Hoogstein binding, or other sequence specific binding known in the art. Hybridisation can be performed under different stringency conditions known in the art. "Specifically hybridises," as used herein, is hybridization that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex" has 19 base pairs. The remaining bases may, for example, exist as 5' and/or 3' overhangs. Further, within the duplex, 100% complementarity is not required; substantial complementarity is allowable within a duplex. Substantial complementarity refers to 75% or greater complementarity. For example, a mismatch in a duplex consisting of 19 base pairs results in 94.7% complementarity, rendering the duplex substantially complementary.

In an embodiment, the oligonucleotide specifically hybridises to an exon, intron or exon-intron boundary target region of an IFN-γ RNA, the target region is any one selected from the group comprising: exon 1 and exon 2.

In other embodiments, the oligonucleotide specifically hybridises to an exon, intron or exon-intron boundary target region of a Perforin, the target region is exon 2b.

In other embodiments, the oligonucleotide specifically hybridises to an exon, intron or exon-intron boundary target region of a Granzyme RNA, the target region is exon 3.

In other embodiments, the oligonucleotide specifically hybridises to an exon, intron or exon-intron boundary target region of a PD-1 RNA, the target region is exon 2.

The antisense oligonucleotide of the present invention may comprise a sequence selected from any one of SEQ ID NOs: 1 to 69575.

As will be discussed later, the sequences of the oligonucleotides (AONs) of the present invention may be modified. An example of the modified sequences is shown in FIG. 24.

In an embodiment, the 35 sequences used in the present invention are sent out in the Table 1 below.

TABLE 1

| | | |
|---|---|---|
| 0615_263_2OM_E2 | IFNG | 5'-GUU CCA UUA UCC GCU ACA UCU GAA UGA CCU GC-3' |
| 0615_264_2OM_E3 | IFNG | 5'-UUU GAA GUA AAA GGA GACAAU UUG GCU CUG CAU U-3' |
| 0615_265_2OM_E3 | IFNG | 5'-UUU UGG AUG CUC UGG UCA UCU UUA AAG UUU UUA-3' |
| 0615_266_2OM_E3 | GZMB | 5'-UAU UGU GGG CCC CCA AGG UGA CAU UUA UG-3' |
| 0615_267_2OM_E3 | GZMB | 5'-UAA ACU GCU GGG UCG GCU CCU GUU CUU UGA-3' |
| 0615_268_2OM_E2b | PFF1 | 5'-UGU AGG GCA UUU UCA CAG AGG GUG CAG GU-3' |
| 0615_269_2OM_E2b | PFF1 | 5'-AUG CCC AGG AGG AGC AGA CGG GCU GCC AUG-3' |
| 0915_315_2OM_E2 | PD-1 | 5'-GUU CCA GGG CCU GUC UGG GG-3' |

TABLE 1-continued

| | | |
|---|---|---|
| 0915_316_2OM_E2 | PD-1 | 5'-AGG GCU GGG GAG AAG GUG GGG-3' |
| 0915_317_2OM_E2 | PD-1 | 5'-AGU UUA GCA CGA AGC UCU CCG AUG UGU-3' |
| 0915_318_2OM_E3 | PD-L1 | 5'-CAC AUA UAG GUC CUU GGG AAC CGU GA-3' |
| 0915_319_2OM_E4 | PD-L1 | 5'-CAG UUC AUG UUC AGA GGU GAC UGG AUCC-3' |
| 0316_442_2OM_E4 | PFDM1 | 5'-AGG UUU UGC UCC CGG GGA GAG U-3' |
| 0316_443_2OM_E4 | PFDM1 | 5'-GGU GAA GCU CCC CUC UGG AAU AGA U-3' |
| 0316_444_2OM_E4 | PFDM1 | 5'-AUG GUG UAG AAG UAG AUG UUC AUC UGC UU-3' |
| 0316_447_2OM_E3 | CD40LG | 5'-UGU UUU CUU UCU UCG UCU CCU CUU UGU UU-3' |
| 0316_448_2OM_E2 | CTLA4 | 5'-AAG GUC AAC UCA UUC CCC AUC AUG UAG GUU G-3' |
| 0316_449_2OM_E2 | CTLA4 | 5'-GUG GCU UUG CCU GGA GAU GCA UA-3' |
| 0316_450_2OM_E2 | CTLA4 | 5'-UUG CCG CAC AGA CUU CAG UCA C-3' |
| 0316_451_2OM_E2 | CTLA4 | 5'-AUG CAU ACU CAC ACA CAA AGC UGG-3' |
| 0316_452_2OM_E3 | NDRP1 | 5'-AUA ACU GGG CAG UGU UGU AGC UAC AUU G-3' |
| 0316_453_2OM_E3 | NDRP1 | 5'-UGG AAA CCC AGA CUC AUC CUU GUA GU-3' |
| 0316_457_2OM_E3 | PDOD1LG2 | 5'-UCC AGU GUC AAA GUU GCA UUC CAG GGU-3' |
| 0316_458_2OM_E4 | PDOD1LG2 | 5'-UCA UCU GUU UCU GGA ACC UUU AGG AUG UGA GU-3' |
| 0316_462_2OM_E2 | FEL | 5'-GGG UUG UUC AAU UAU CUC UAU AUA AGG GU-3' |
| 0316_463_2OM_E3 | FEL | 5'-GGU UUA UAU GGG UCA UUC UUU GUU ACU AA-3' |
| 0316_464_2OM_E3 | FEL | 5'-UAG UAG CCG UCU CUG GAG UCU UUU C-3' |
| 0616_520_2OM_E2 | BTLA | 5'-UGC UAA GAU GGA GUG UUC AGA UUG UCU CUU UAU A-3' |
| 0616_521_2OM_E4 | BTLA | 5'-AAU UUC CCU UCC UGC UGU GUC AGA GAG-3' |
| 0616_522_2OM_E2 | CD80 | 5'-UGG GUC UCC AAA GGU UGU GGA UUU AGU UU-3' |
| 0616_523_2OM_E3 | CD160 | 5'-AAC UUG AAG CAA AUG UUG GCU CUG CUG GUA-3' |
| 0616_524_2OM_E5 | CD244 | 5'UCG UAA AUU GUC AAA AUC CUU GGA CUG GUC U-3' |
| 0616_525_2OM_E2 | LAG3 | 5'-GAG AUC CUG GAG GGG GAU UGU GG-3' |
| 0616_526_2OM_E3 | TIGIT | 5'-AAU GGA AUC UGG AAC CUG GCA CCG U-3' |
| 0616_527_2OM_E4 | TIM-3 | 5'-AUU UAU AUC AGG GAG GCU CCC CAG UG-3' |

Table 2 sets out the corresponding SEQ ID Nos set out in the sequence listing that corresponds to the sequences of Table 1.

TABLE 2

| Sequence Listing | SEQ ID Nos. in Table 1 | SEQ ID Nos. set out in sequence listing |
|---|---|---|
| guuccauuauccgcuacaucugaaugaccugc | 1 | 7274 |
| uuugaaguaaaaggagacaauuuggcucugcauu | 2 | 7970 |
| uuuuggaugcucuggucaucuuuaaaguuuuua | 3 | 8521 |
| uauugugggccccccaaggugacauuuaug | 4 | 11414 |
| uaaacugcugggucggcuccuguucuuuga | 5 | 11514 |

TABLE 2-continued

| Sequence Listing | SEQ ID Nos. in Table 1 | SEQ ID Nos. set out in sequence listing |
|---|---|---|
| uguagggcauuuucacagagggugcaggu | 6 | 15372 |
| augcccaggaggagcagacgggcugccaug | 7 | 15458 |
| guuccagggccugucugggg | 8 | 3680 |
| agggcuggggagaagguggggg | 9 | 3817 |
| aguuuagcacgaagcucuccgaugugu | 10 | 3877 |
| cacauauagguccuugggaaccguga | 11 | 19411 |

TABLE 2-continued

| Sequence Listing | SEQ ID Nos. in Table 1 | SEQ ID Nos. set out in sequence listing |
|---|---|---|
| caguucauguucagaggugacuggaucc | 12 | 20993 |
| agguuuugcucccggggagagu | 13 | 25333 |
| ggugaagcuccccucuggaauagau | 14 | 25599 |
| augguguagaaguagauguucaucccguu | 15 | 25676 |
| uguuucuuucuucgucuccucuuuguuu | 16 | 32803 |
| aaggucaacucauucccaucauguagguug | 17 | 400 |
| guggcuuugccuggagaugcaua | 18 | 1073 |
| uugccgcacagacuucagucac | 19 | 1097 |
| augcauacucacacacaaagcugg | 20 | 1684 |
| auaacugggcaguguuguagcuacauug | 21 | 35585 |
| uggaaacccagacucauccuuguagu | 22 | 35761 |
| uccagugucaaaguugcauuccagggu | 23 | 40204 |
| ucaucuguuucuggaaccuuuaggaugugagu | 24 | 42491 |
| gggguguucaauuaucucuauauacgggu | 25 | 43942 |
| gguuuauaugggucauucuuuguuacuaa | 26 | 45170 |
| uaguagccgucucugcagucuuuuc | 27 | 45445 |
| ugcuaagauggagguucagauugucucuuuaua | 28 | 46162 |
| aauuucccuuccugcuguguucagagag | 29 | 53243 |
| ugggucuccaaagguuguggauuuaguuu | 30 | 53882 |
| aacuugaagcaaauguuggcucugcuggua | 31 | #N/A |
| ucguaaauugucaaaaauuccuugggacuggucu | 32 | 63352 |
| gagauccuggaggggggauugugg | 33 | 63703 |
| aauggaaucuggaaccuggcaccgu | 34 | 66260 |
| auuuauaucagggaggcuccccagug | 35 | 67190 |

In an embodiment, the present invention provides for an oligonucleotide having any one of the following sequences: SEQ ID NOs: 6508, 69648, 2565, 7274, 15372, 63352, 67190, 66260, 25333, 25599, 25676, 43942, 45170, 45445, 61632 and 53882.

By "oligonucleotide", it is meant to refer to any polynucleotide. A "polynucleotide" is an oligomer comprised of nucleotides. A polynucleotide may be comprised of DNA, RNA modified forms thereof, or a combination thereof. The term "nucleotide" or its plural as used herein is interchangeable with modified forms as discussed herein and otherwise known in the art. In certain instances, the art uses the term "nucleobase" which embraces naturally occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6- methyladenine, 7-deazaxanthine, 7-deazaguanine, N4,N4-ethanocytosin, N',N'-ethano-2,6-diaminopurine, 5-methylcytosine (mC), 5-(C[3]- C6)-alky- nyl-cytosine, 5-fluorouracil, 5- bromouracil, pseudoisocytosine, 2-hydroxy-5-methyl-4-triazolopyridin, isocytosine, isoguanine, inosine and the "non-naturally occurring" nucleobases described in Benner et ah, U. S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et ah), in Chapter 15 by Sanghvi, in Antisense Research and Application, Ed. S. T. Crooke and B. Lebleu, CRC Press, 1993, in Englisch et ah, 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which is hereby incorporated by reference in its entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles {e.g., 5-nitroindole), and optionally substituted hypoxanthine. Other desirable universal bases include pyrrole, and diazole or triazole derivatives, including those universal bases known in the art.

Polynucleotides may also include modified nucleobases. A "modified base" is understood in the art to be one that can pair with a natural base {e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include, without limitation, 5- methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8- thioalkyl, 8-hydroxyl and other 8-substituted adenines and guanines, 5-halo particularly 5- bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b] [1,4]benzoxazin-2(3H)- one), phenothiazine cytidine (1H-pyrimido[5,4-b] [1,4]benzothiazin-2(3H)-one), G-clamps such as a substituted phenoxazine cytidine (e.g. 9-(2-aminoethoxy)-H-pyrimido[5,4-b] [1,4] benzox-azin-2(3H)-one), carbazole cytidine (2H-pyrimido [4,5-b]indol-2-one), pyridoindole cytidine (H- pyrido[3',2': 4,5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Additional nucleobases include those disclosed in U. S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et ah, 1991, Angewandte Chemie, International Edition, 30: 613, and those disclosed by Sanghvi, Y. S., Chapter 15, Antisense Research and Applications, pages 289- 302, Crooke, S. T. and Lebleu, B., ed., CRC Press, 1993. Certain of these bases are useful for increasing the binding affinity of the polynucleotide and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.deg.C. and are, in certain aspects, combined with 2'- O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Those of skill in the art can readily design antisense polynucleotides according to the present disclosure. For example, general teachings in the art include, but are not limited to, Aartsma-Rus et al, Methods Mol Biol. 867: 117-29 (2012); Aartsma-Rus et al, Methods Mol Biol. 867: 97-116 (2012); van Roon-Mom et al., Methods Mol Biol. 867: 79-96 (2012), each of which is incorporated herein by reference. General guidelines also include attempting to avoid 3 consecutive G or C nucleotides, choosing lengths and sequences that favour self structure (hairpinning will be avoided), and avoiding those sequences likely to form primer dimers. In some embodiments, an antisense polynucleotide of the disclosure is one that is designed to specifically hybridize to an exon or an intron or an intron-exon boundary, such that the antisense polynucleotide specifically hybridises to a sequence that is completely within an exon of an immune-related or immunomodulatory genes/ nucleic acid expressed by the T-cell, or about one nucleotide of the antisense polynucleotide spans said intron-exon boundary when the antisense polynucleotide is specifically hybridised to such a nucleic acid. In some embodiments wherein the antisense polynucleotide specifically hybridizes to a sequence that is completely within an exon, it is contemplated that a terminus of the antisense polynucleotide is about 1, 2, 3, 4, 5, 6, 7, 8, 9, 10 or more nucleotides from a terminus of the exon.

Modified polynucleotides are contemplated for use wherein both one or more sugar and/or one or more internucleotide linkage of the nucleotide units in the polynucleotide is replaced with "non-naturally occurring" sugars (i.e., sugars other than ribose or deoxyribose) or internucleotide linkages, respectively. In one aspect, this embodiment contemplates a peptide nucleic acid (PNA). In PNA compounds, the sugar-backbone of a polynucleotide is replaced with an amide-containing (e.g., peptide bonds between N-(2-aminoethyl)-glycine units) backbone. See, for example U. S. Pat. Nos. 5,539,082; 5,714,331; and 5,719,262, and Nielsen et ah, Science, 1991, 254, 1497- 1500, the disclosures of which are herein incorporated by reference. Modified polynucleotides may also contain one or more substituted sugar groups. In one aspect, a modification of the sugar includes Locked Nucleic Acids (LNAs) in which the 2'- hydroxyl group is linked to the 3' or 4' carbon atom of the sugar ring, thereby forming a bicyclic sugar group. The linkage is in certain aspects a methylene (—$CH_{[2]}$—)$_{[n]}$ group bridging the 2' oxygen atom and the 4' carbon atom wherein n is 1 or 2. LNAs and preparation thereof are described in WO 98/39352 and WO 99/14226, the disclosures of which are incorporated herein by reference. In the present invention, preferably, the antisense oligonucleotide comprises a modified polynucleotide backbone. The modified polynucleotide backbone may comprise a modified moiety substituted for the sugar of at least one of the polynucleotides.

In various embodiments, the antisense oligonucleotide comprising a modified polynucleotide backbone. The modified polynucleotide backbone may comprises a modified moiety substituted for the sugar of at least one of the polynucleotides. The modified moiety may be selected from the group consisting of phosphorodiamidate morpholino oligomer (PMO), peptide-conjugated phosphorodiamidate morpholino oligomer (PPMO), and non-peptide dendrimeric octaguanidine moiety-tagged morpholino oligomer.

In various embodiments, the modified polynucleotide backbone may comprise at least one modified internucleotide linkage. The modified internucleotide linkage may comprise a modified phosphate. The modified phosphate is selected from the group comprising of a non-bridging oxygen atom substituting a sulfur atom, a phosphonate, a phosphorothioate, a phosphodiester, a phosphoromorpholidate, a phosphoropiperazidate and a phosphoroamidate.

In various embodiments, the antisense oligonucleotide comprises a backbone which is selected from the group comprising of ribonucleic acid, deoxyribonucleic acid, DNA phosphorothioate, RNA phosphorothioate, 2'-O-methyl-oligoribonucleotide and 2'-O-methyl-oligodeoxyribonucleotide, 2'-O-hydrocarbyl ribonucleic acid, 2'-O-hydrocarbyl DNA, 2'-O-hydrocarbyl RNA phosphorothioate, 2'-O-hydrocarbyl DNA phosphorothioate, 2'-F-phosphorothioate, 2'-F-phosphodiester, 2'-methoxyethyl phosphorothioate, 2-methoxyethyl phosphodiester, deoxy methylene(methylimino) (deoxy MMI), 2'-O-hydrocarby MMI, deoxy-methylphos-phonate, 2'-O-hydrocarbyl methylphosphonate, morpholino, 4'-thio DNA, 4'-thio RNA, peptide nucleic acid, 3'-amidate, deoxy 3'-amidate, 2'-O-hydrocarbyl 3'-amidate, locked nucleic acid, cyclohexane nucleic acid, tricycle-DNA, 2'fluoro-arabino nucleic acid, N3'-P5' phosphoroamidate, carbamate linked, phosphotriester linked, a nylon backbone modification and mixtures of the aforementioned backbones.

In various embodiments, the oligonucleotide is chemically linked to one or more conjugates that enhance the activity, cellular distribution, or cellular uptake of the antisense oligonucleotide.

The oligonucleotide may be chemically linked to one or more conjugates that enhance the activity, cellular distribution, or cellular uptake of the antisense oligonucleotide.

The compounds of the disclosure also can be used as a prophylactic or therapeutic, which may be utilized for the purpose of treatment of a genetic disease. Hence, advantageously, the antisense oligonucleotide according to the present invention may be used in treating cancer, or an autoimmune disease in a patient. In addition to the antisense oligonucleotide, the patient may be administered a further anti-cancer agent or treatment. The cancer may be any one selected from the group comprising: HBV induced HCC, EBV induced Non Hodgkin Lymphomas.

As such, the antisense oligonucleotide of the present invention may be used to prepare novel chemical formulas for highly efficacious (IC50<2.5 nM) drug candidates against immunomodulatory molecules (e.g. IFN-gamma, Granzyme, Perforin1 etc). In another aspect of the present invention, there is provided a pharmaceutical composition comprising the antisense oligonucleotide according to the present invention and a pharmaceutically acceptable carrier.

A pharmaceutically acceptable carrier refers, generally, to materials that are suitable for administration to a subject wherein the carrier is not biologically harmful, or otherwise, causes undesirable effects. Such carriers are typically inert ingredients of a medicament. Typically a carrier is administered to a subject along with an active ingredient without causing any undesirable biological effects or interacting in a deleterious manner with any of the other components of a pharmaceutical composition in which it is contained. Suitable pharmaceutical carriers are described in Martin, Remington's Pharmaceutical Sciences, 18th Ed., Mack Publishing Co., Easton, Pa., (1990), incorporated by reference herein in its entirety.

In a more specific form of the disclosure there are provided pharmaceutical compositions comprising therapeutically effective amounts of an antisense polynucleotide together with pharmaceutically acceptable diluents, preservatives, solubilizers, emulsifiers, adjuvants and/or carriers. Such compositions include diluents of various buffer content (e.g., phosphate, Tris-HCl, acetate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as, for example and without limitation, polylactic acid or polyglycolic acid, or into liposomes. Hylauronic acid may also be used. Such compositions may influence the physical state, stability, rate of in vivo release, and rate of in vivo clearance of the disclosed compositions. The compositions may be prepared in liquid form, or may be in dried powder, such as lyophilized form.

It will be appreciated that pharmaceutical compositions provided according to the disclosure may be administered by any means known in the art. Preferably, the pharmaceutical compositions for administration are administered by injection, orally, or by the pulmonary, or nasal route. The antisense polynucleotides are, in various embodiments, delivered by intravenous, intra-arterial, intraperitoneal, intramuscular, or subcutaneous routes of administration. In various embodiments, the composition is suitable for parenteral administration either naked or complexed with a delivery agent to a patient. The carrier may be selected from the group comprising of a nanoparticle, such as a polymeric nanoparticle; a liposome, such as pH-sensitive liposome, an antibody conjugated liposome; a viral vector, a cationic lipid, a polymer, a UsnRNA, such as U7 snRNA and a cell penetrating peptide.

The antisense oligonucleotide may be administered orally, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular.

The antisense molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For polynucleotides, preferred examples of pharmaceutically acceptable salts include, but are not limited to, (a) salts formed with cations such as sodium, potassium, ammonium, magnesium, calcium, polyamines such as spermine and spermidine; (b) acid addition salts formed with inorganic acids, for example hydrochloric acid, hydrobromic acid, sulfuric acid, phosphoric acid, nitric acid; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid; and (d) salts formed from elemental anions such as chlorine, bromine, and iodine. The pharmaceutical compositions of the disclosure may be administered in a number of ways depending upon whether local or systemic treatment is desired and upon the area to be treated. Administration may be topical (including ophthalmic and to mucous membranes including rectal delivery), pulmonary, e.g., by inhalation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Polynucleotides with at least one 2'-O-methoxyethyl modification are believed to be particularly useful for oral administration.

The pharmaceutical formulations of the disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly bringing into association the active ingredients with liquid carriers or finely divided solid carriers or both, and then, if necessary, shaping the product.

Combination therapy with an additional therapeutic agent is also contemplated by the disclosure. Examples of therapeutic agents that may be delivered concomitantly with a composition of the disclosure include, without limitation, a glucocorticoid steroid (for example and without limitation, prednisone and deflazacort), an angiotensin converting enzyme inhibitor, a beta adrenergic receptor blocker, an anti-fibrotic agent and a combination thereof.

In some embodiments, the present invention may be used in gene therapy such, e.g. using a vector (e.g., an expression vector) comprising a polynucleotide of the invention to direct expression of the polynucleotide in a suitable host cell. Such vectors are useful, e.g., for amplifying the polynucleotides in host cells to create useful quantities thereof, and for expressing proteins using recombinant techniques. In some embodiments, the vector is an expression vector wherein a polynucleotide of the invention is operatively linked to a polynucleotide comprising an expression control sequence.

In various embodiments, the composition comprising an oligonucleotide of the present invention may further comprise a nucleic acid molecule that encodes a T-cell receptor gene. In an embodiment, the nucleic acid molecule may be an mRNA molecule.

Methods for introducing a nucleic into the T-cell, which are well known and routinely practiced in the art, include transformation, transfection, electroporation, nuclear injection, or fusion with carriers such as liposomes, micelles, ghost cells, and protoplasts. The host T-cell may be isolated and/or purified. The T-cell also may be a cell transformed in vivo to cause transient or permanent expression of the polypeptide in vivo. The T-cell may also be an isolated cell transformed ex vivo and introduced post-transformation, e.g., to produce the polypeptide in vivo for therapeutic purposes.

The ASOs of the present invention may be introduced into a T cell by methods of transfection well known in the art. These methods include sonophoresis, electric pulsing, electroporation, osmotic shock, calcium phosphate precipitation, and DEAE dextran transfection, lipid mediated delivery, passive delivery etc. The language "transfecting T cells" is intended to include any means by which a nucleic acid molecule can be introduced into a T cell. The term "transfection" encompasses a variety of techniques useful for introduction of nucleic acids into mammalian cells including electroporation, calcium-phosphate precipitation, DEAE-dextran treatment, lipofection, microinjection, and viral infection. Suitable methods for transfecting mammalian cells can be found in Sambrook et al. (*Molecular Cloning: A Laboratory Manual, 2nd Edition*, Cold Spring Harbor Laboratory press (1989)) and other laboratory textbooks.

The ASO may also be introduced into a I cell using a viral vector. Such viral vectors include, for example, recombinant retroviruses, adenovirus, adeno-associated virus, and herpes simplex virus-1. Retrovirus vectors and adeno-associated virus vectors are generally understood to be the recombinant gene delivery system of choice for the transfer of exogenous genes in vivo, particularly into humans. Alternatively they can be used for introducing exogenous genes ex vivo into T cells. These vectors provide efficient delivery of genes into T cells, and the transferred nucleic acids are stably integrated into the chromosomal DNA of the host cell.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. Yet another viral vector system useful for delivery of a nucleic acid molecule comprising a gene of interest is the adeno-associated virus.

The ASOs may be carried by and delivered into a T cell by a cell-delivery vehicle. Such vehicles include, for example, cationic liposomes (Lipofectin™) or derivatized (e.g. antibody conjugated) polylysine conjugates, gramicidin S, artificial viral envelopes. These vehicles can deliver a nucleic acid that is incorporated into a plasmid, vector, or viral DNA. In a specific embodiment, efficient introduction of the nucleic acid molecule in primary T lymphocytes is obtained by transfecting the primary T lymphocytes with adeno-associated virus plasmid DNA complexed to cationic liposomes, as described in Philip, R. et al. (1994) *Mol. Cell. Biol.* 14, 2411.

In another embodiment of the invention, the ASOs may be delivered in the form of a soluble molecular complex. The complex contains the nucleic acid releasably bound to a carrier comprised of a nucleic acid binding agent and a cell-specific binding agent which binds to a surface molecule of the specific T cell and is of a size that can be subsequently internalized by the cell.

In another embodiment of the invention the nucleic acid is introduced into T cells by particle bombardment.

In various embodiments, the ASOs may be passively delivered (i.e., deliver without additional transfection reagents) to the T cells, particularly during T cell expansion. Expansion as used herein includes the production of progeny cells by a transfected neural stem cell in containers and under conditions well know in the art. Expansion may occur in the presence of suitable media and cellular growth factors. The ASOs may be passively delivered to the T cells in culture (e.g., in culture plates, culture dishes, multiwell plates etc without limitation) under reduced serum conditions, including under 0% serum conditions. Such conditions include cells cultured in standard, art-tested reduced-serum media that are commercially available from numerous companies including Invitrogen, and HyClone. In one example, cells are first plated in serum medium, then the serum medium is replaced with reduced serum medium comprising a tripartite oligonucleotide complex of the disclosure for 24 hours, then the reduced serum medium is replaced with serum medium.

In various embodiments, the transfection reagent may be selected from the group consisting of polymers, lipids, lipid-polymers and/or their combinations and/or their derivatives containing a cell-targeting or an intracellular targeting moiety and/or a membrane-destabilizing component and one or more delivery enhancers.

In another aspect of the present invention, there is provided a method of treating a disease in a patient, the method comprising administering an antisense oligonucleotide according to the present invention or a pharmaceutically effective amount of a composition according to the present invention.

The term "effective amount" or "therapeutically effective amount" means a dosage sufficient to treat, inhibit, or alleviate one or more symptoms of a disease state being treated or to otherwise provide a desired pharmacologic and/or physiologic effect, especially enhancing T cell response to a selected antigen. The precise dosage will vary according to a variety of factors such as subject-dependent variables (e.g., age, immune system health, etc.), the disease, and the treatment being administered.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

The antisense oligonucleotide or composition may be administered orally, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular. Having said that, proven systemic administration options include intravenous, intraperitoneal, intranasal and intrathecal. Complexing of ASOs with delivery carriers such as nanoparticles, polymer- or liposome-based vehicles can further augment the delivery efficiency of ASOs to specific tissues.

In various embodiments, the antisense oligonucleotide has been transfected in a T cell, and the method comprising administering the transfected T cell to the patient. The antisense oligonucleotide may be transfected or introduced to the T cell by an electroporation process.

Alternatively, the introduction of the oligonucleotides of the present invention into the T-cell can be effected by calcium phosphate transfection, DEAF-dextran mediated transfection, cationic lipid-mediated transfection, transduction, infection, microinjection, recombinant viral and retroviral infection or other methods. Such methods are described in many standard laboratory manuals, such as Davis et al., Basic Methods 1n Molecular Biology (1986). It is specifically contemplated that the polypeptides of the present invention may in fact be expressed by a host cell lacking a recombinant vector.

In various embodiments, the carrier is selected from the group consisting of a nanoparticle, such as a polymeric nanoparticle; a liposome, such as pH-sensitive liposome, an antibody conjugated liposome; a viral vector, a cationic lipid, a polymer, a UsnRNA, such as U7 snRNA and a cell penetrating peptide.

In various embodiments, the antisense oligonucleotide or composition is administered orally, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular.

The disease may be a cancer selected from the group comprising: HBV induced HCC, EBV induced Non Hodgkin Lymphomas.

As such, it is the antisense oligonucleotide according to the present invention is useful in medicine.

In another aspect of the present invention, there is provided a method of inducing exon-skipping of an immune-related or immunomodulatory genes pre-mRNA expressed by the T-cell, the method comprising delivering to a cell an antisense oligonucleotide or a composition according to any one of the above aspects of the present invention.

In various embodiments, the cell is a human cell.

In another aspect of the present invention, there is provided a method for modulating the function of a T-cell, the method comprising administering to the T-cell an antisense oligonucleotide according to the present invention.

The method further comprising modifying the specificity of the T-cell by administering to the T-cell a nucleic acid molecule that encodes a T-cell receptor gene. The nucleic acid molecule that encodes a T-cell receptor gene is transfected or introduced to the T cell by electroporation.

In yet another aspect of the present invention, there is provided a T-cell transformed or transfected with an antisense oligonucleotide according to the present invention. In various embodiments, the antisense oligonucleotide is transfected or introduced to the T cell by an electroporation process.

The T-cell may further comprise a nucleic acid molecule that encodes a T-cell receptor gene, wherein the nucleic acid molecule is an mRNA.

In yet another aspect of the present invention, there is provided a kit comprising the antisense oligonucleotide according to the present invention, optionally in a container, and a package insert, package label, instructions or other labelling.

In order that the present invention may be fully understood and readily put into practical effect, there shall now be described by way of non-limitative examples only preferred embodiments of the present invention, the description being with reference to the accompanying illustrative figures.

In the Figures:

FIG. 1. Flow cytometry plots showing non transfected T-cells (left), T-cells transfected with an ASO tagged with FAM (centre) and T-cells transfected with an HBV-specific TCR together with the FAM-tagged ASO (right). The TCR is stained using a PE (phycoerythrin)-conjugated pentamer while the ASO is tagged with FAM (6-carboxyfluorescein).

Figure 2:
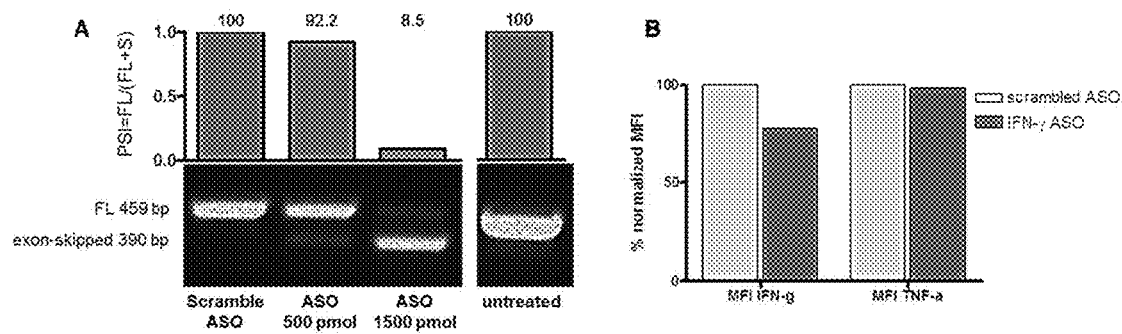

FIG. 2. A. Lower part: PCR reaction amplifying IFN-γ mRNA in T-cells treated with a scrambled ASO (left), 500 picomoles of a IFN-γ specific ASO (centre) or 1500 picomoles of the same ASO (right). The separated lane shows the amplification of IFN-γ mRNA in not electroporated T-cells. Upper part: histogram bars representing the PSI (Percentage Spliced Index) of the full-length transcript. The PSI provides the inclusion level of the analysed exon. B. Histogram bars showing MFI of IFN-γ and TNF-α fluorescent staining (median fluorescence intensity) normalized to the MFI of scrambled ASO-treated T-cells from intracellular cytokine staining.

Figure 3:
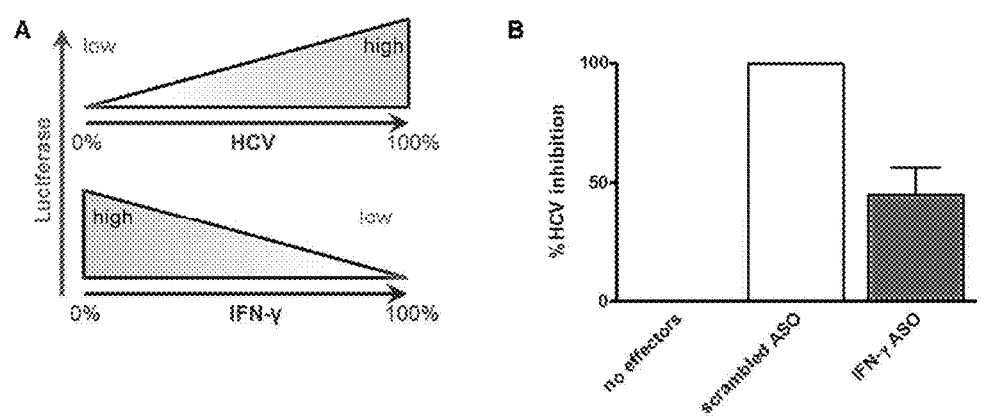

FIG. 3. A. Luciferase expression in the HuH7 HCV-replicon cell line in relation to HCV replication or IFN-γ concentration in the culture medium. B. Histogram bars representing the percentage of HCV inhibition in HuH7 HCV-replicon cell line by IFN-γ-ASO treated T-cells normalized to the inhibition by scrambled ASO-treated T-cells.

Figure 4:
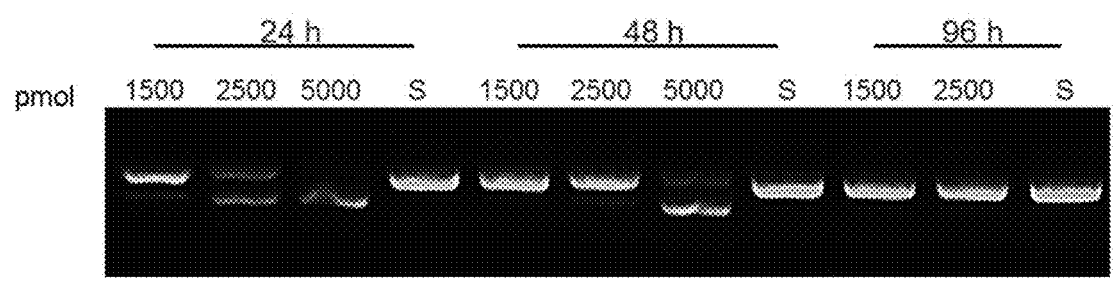

FIG. 4. PCR amplification of IFN-γ mRNA 24-48-96 hours after electroporation of different amounts (1500-2500-5000 picomoles) of IFN-γ specific ASO or a scrambled ASO (2500 picomoles).

Figure 5:
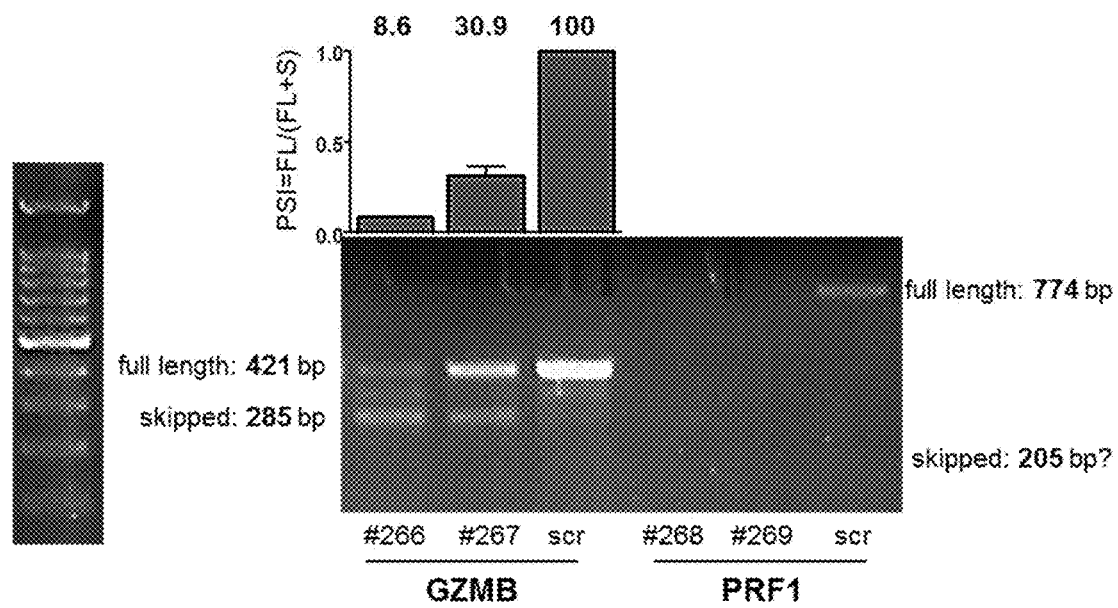

FIG. 5. PCR amplification of granzyme B (GZMB) and perforin (PRF1) mRNA 24 hours after electroporation of 2500 picomoles of granzyme B specific ASOs (#266 or #267), perforin specific ASOs (#268 or #269) or a scrambled ASO. The full length PCR product and the expected exon-skipped product lengths are annotated for both GZMB (left) and PRF1 (right). Upper part: histogram bars representing the PSI of granzyme exon-skip reaction. The same measurement cannot be conducted for perforin, as the specific bands are not detected in the gel.

Figure 6:
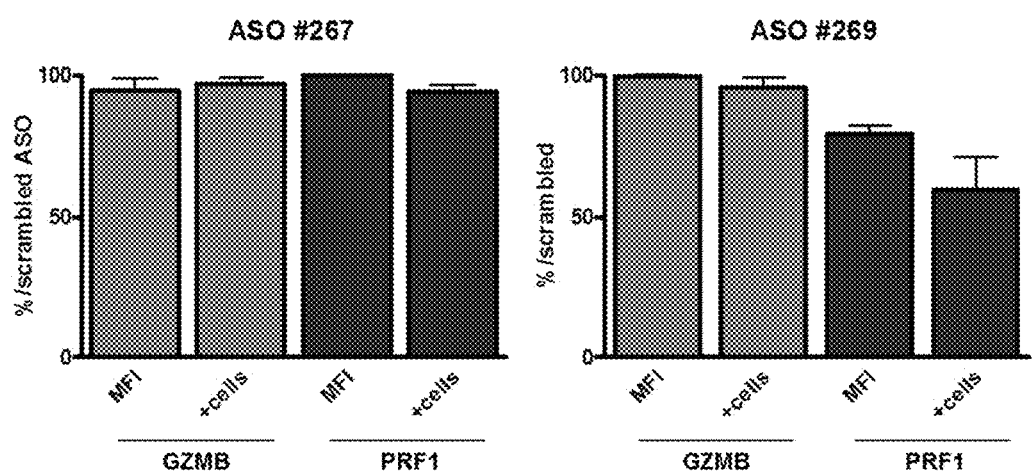

FIG. 6. Histogram bars representing the MFI or the percentage of positive cells in an intracellular cytokine staining experiment in T-cells electroporated with an ASO targeting granzyme B pre-mRNA (left) or perforin pre-mRNA (right). The values are normalized to the values obtained from T-cells electroporated with a scrambled ASO.

Figure 7:
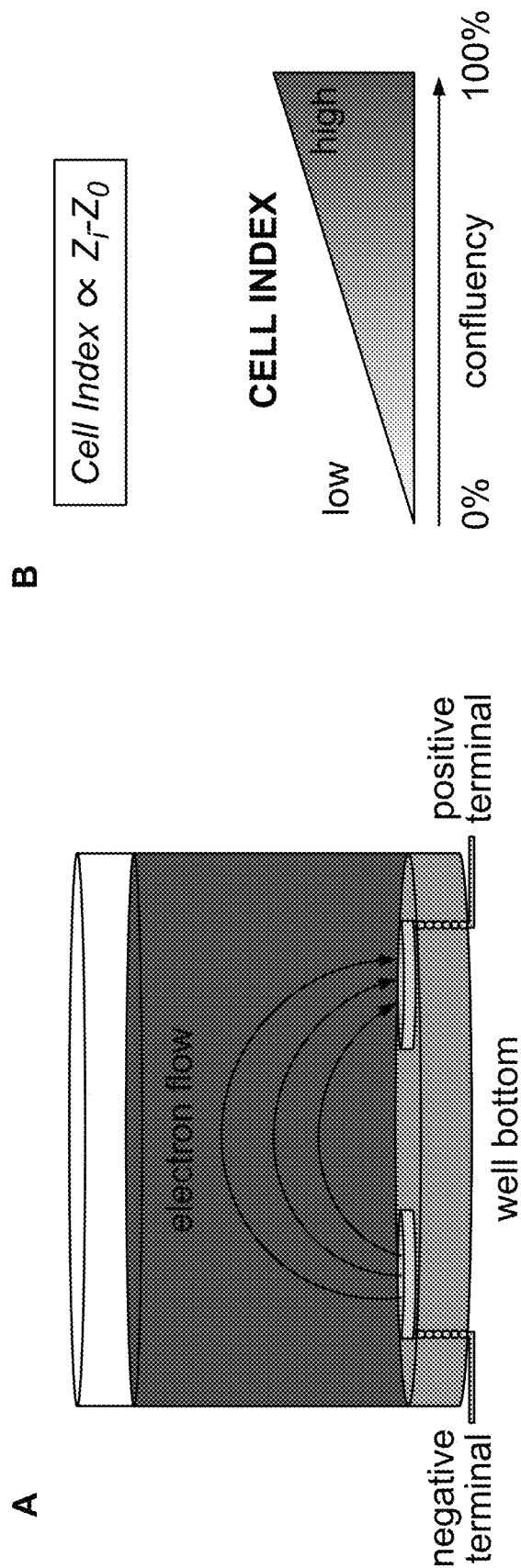

FIG. 7. A. Representation of a well of xCELLigence® RTCA DP. B. Cell Index is a measure-less unit proportional to the impedance measured in the well, which in turn is proportional to the cell confluency.

Figure 8:
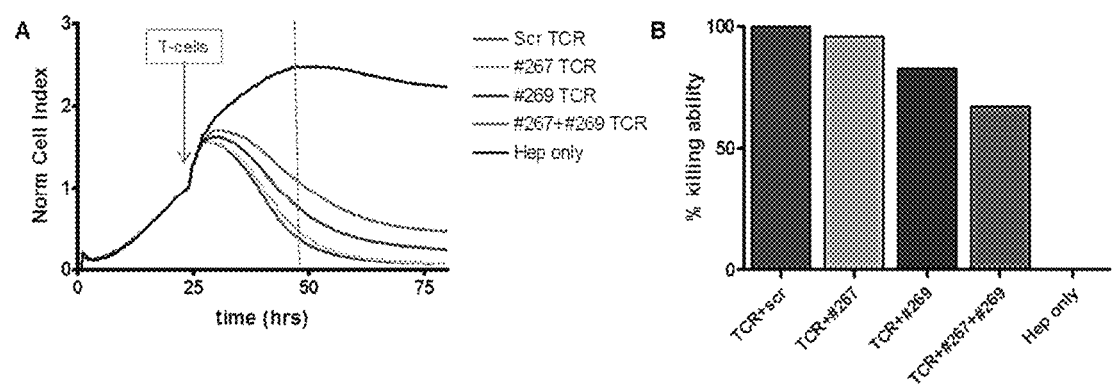

FIG. 8. A. Cell Index plotted over time obtained with xCELLigence®RTCA DP. A HBV-producing hepatoma cell line was seeded on the sensing wells and the cell growth was monitored over 24 hours. HBV-specific TCR-redirected T-cells treated were added in culture (1:2 effector:target ratio) and their cytotoxic ability was measured. T-cells were pre-treated with a scrambled ASO (red), an ASO targeting perforin (green), two ASOs targeting granzyme and perforin (blue and yellow line). The black line represents the Cell Index recorded in wells with no T-cells added. All the Cell Indexes are normalized to the moment in which the T-cells are added in culture. B. Histogram bars representing the cytotoxic ability of HBV-specific TCR-redirected T-cells after 24 hours in culture with HBV-producing hepatoma cell line.

Figure 9:
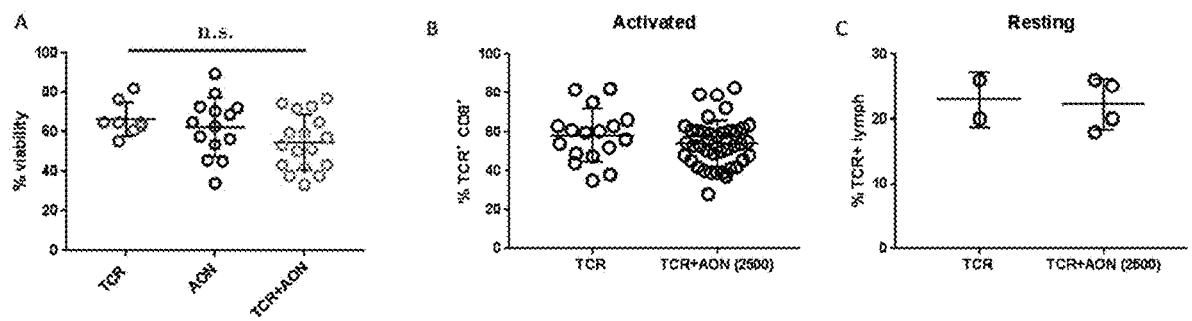
Figure 10:
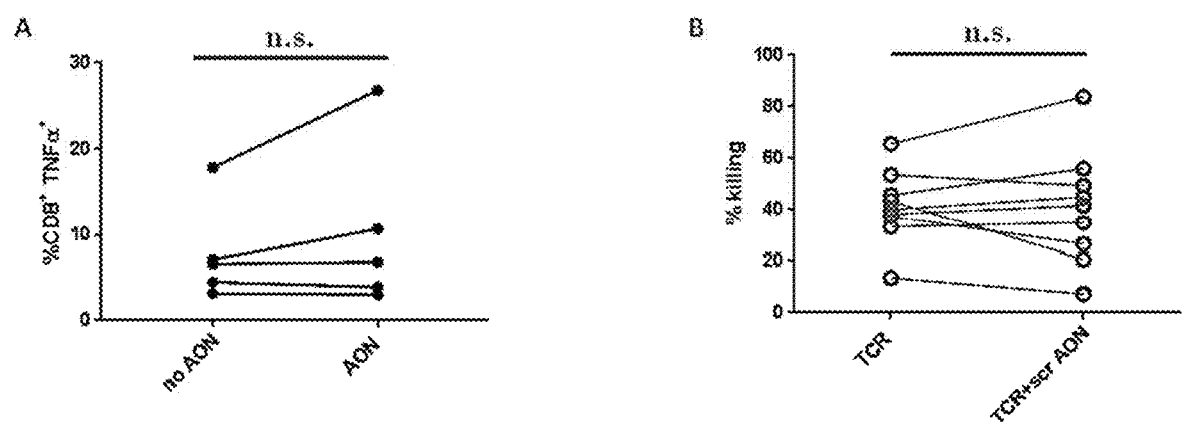

FIGS. 9 and 10. Data from control experiments.

FIGS. 11 to 15. Data obtained from experiments using AONs #887 (SEQ ID NO. 6508), 888 (SEQ ID NO. 69648) and 1173 (SEQ ID NO. 2565) (for targets PD-1 and CTLA-4).

Figure 16:
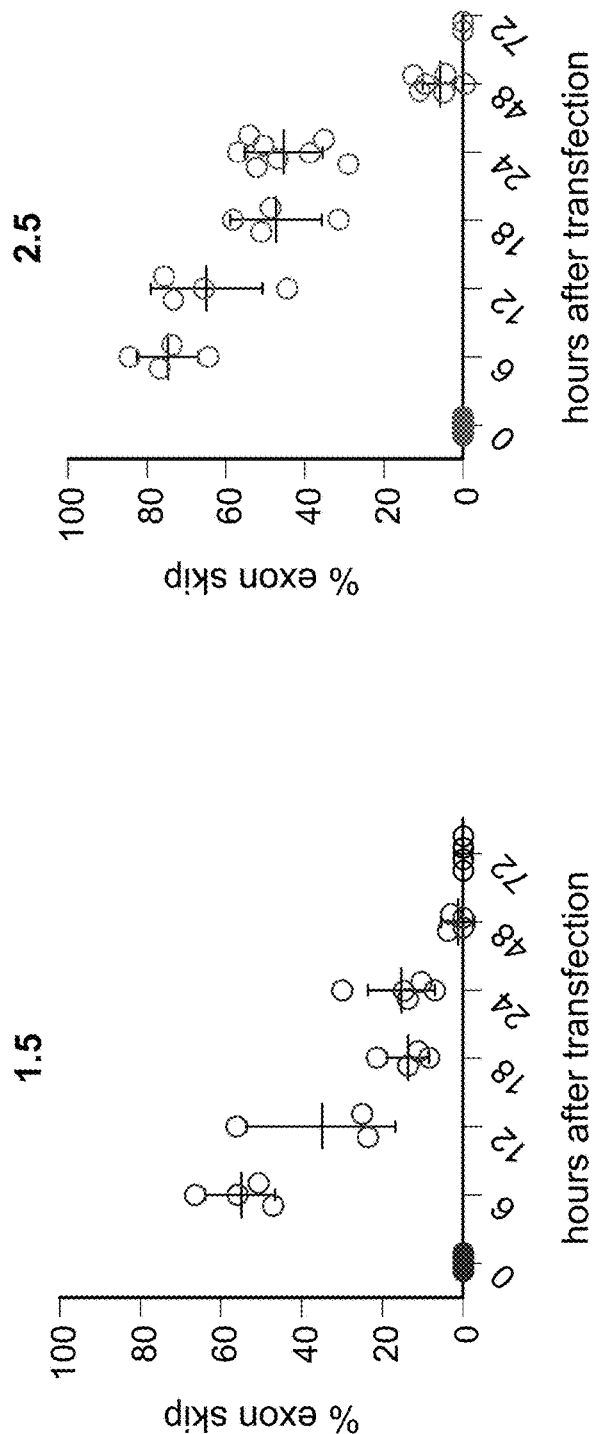
Figure 16:
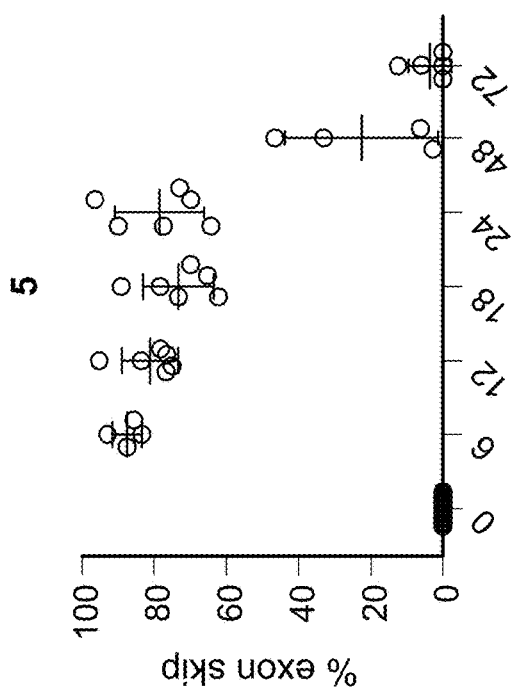

FIGS. 16 and 17. Data obtained from experiments using AON #263 (SEQ ID NO. 7274) (for target IFN-γ).

FIGS. 18 and 19. Data obtained from experiments using AON #268 (SEQ ID NO. 15372) (for target Perforin).

Figure 20:
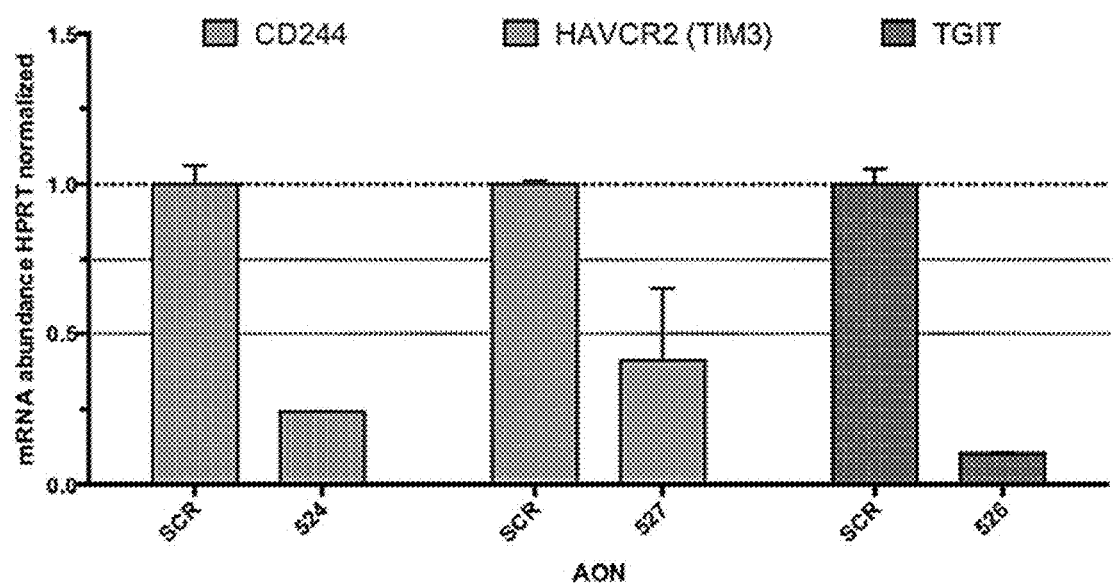

FIG. 20. Data obtained from experiments using AONs #524 (SEQ ID NO. 63352), 527 (SEQ ID NO. 67190) and 526 (SEQ ID NO. 66260) (for targets CD244, TIM3 (HAVCR2) and TGIT).

Figure 21:
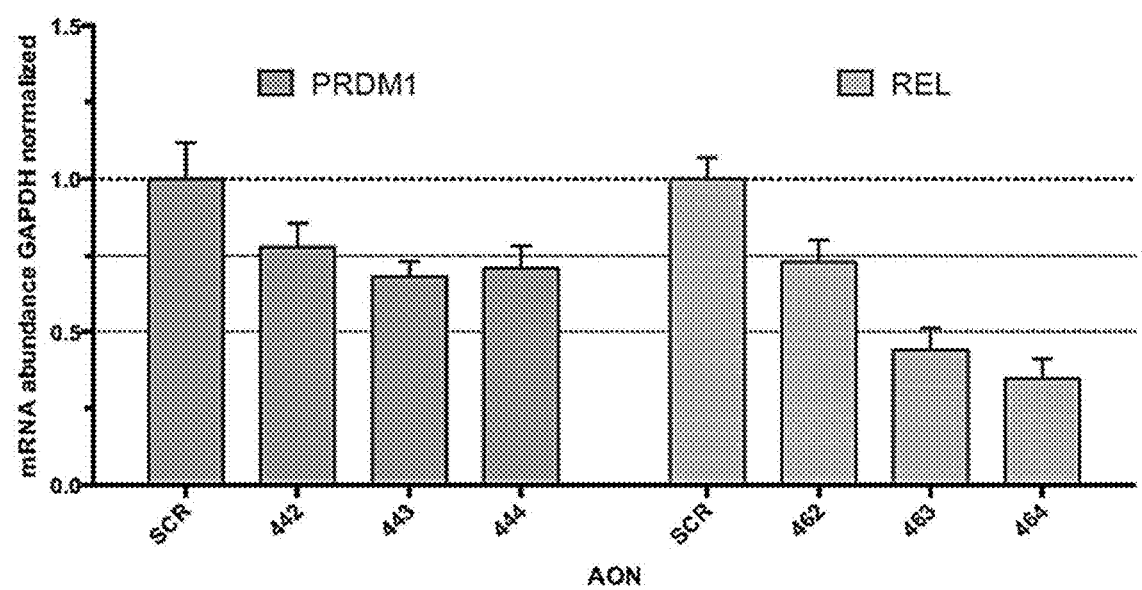

FIG. 21. Data obtained from experiments using AONs #442 (SEQ ID NO. 25333), 443 (SEQ ID NO. 25599), 444 (SEQ ID NO. 25676), 462 (SEQ ID NO. 43942), 463 (SEQ ID NO. 45170) and 464 (SEQ ID NO. 45445) (for targets PRDM1 and REL).

FIG. 22. Data obtained from experiments using AONs #523 (SEQ ID NO. 61632) (for target CD160).

FIG. 23. Data obtained from experiments using AON 522 (SEQ ID NO. 53882) (for target CD80).

FIG. 24 shows an example of a modified sequence according to an embodiment of the present invention.

The present application relates to the field of immunotherapy, specifically to that of immunotherapy directed against tumors and/or viral infections (such as Hepatitis B induced Hepatocellular Carcinoma, EBV induced NKT cell Lymphmas etc.). It is here shown that direct and selective downregulation of immune-related or immunomodulatory genes expressed by T cells [e.g. by Antisense OligoNucleotide (ASO)-mediated exon skipping or intron retention], leads to modulation of T cell functions (such as direct inhibition of viral replication or selective killing of cells expressing a targeted antigen).

Definitions

The present invention will be described with respect to particular embodiments and with reference to certain drawings, but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, New York (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

EXAMPLE 1

ASOs Can Be Efficiently Introduced Into HBV-specific, TCR-Redirected Primary T Cells.

In order to modify the specificity of primary T-cells, we transfected them, using electroporation method, with mRNA coding for the V alpha/beta chain of a TCR recognizing a peptide (S183-191) in the envelope protein of HBV, as in [9]. This peptide is commonly presented via MHC-I on the surface of antigen presenting cells (APCs) or on HBV infected hepatocytes. Therefore, the expression of a S183-191 specific TCR on the surface of the T-cells, make them capable of recognizing the presence of HBV and to undergo, eventually, TCR activation. The expression of the HBV-specific TCR on the surface of T-cells can be assessed using simple surface staining with MHC multimers and flow cytometry analysis. MHC multimers are labelled oligomeric forms of MHC molecules, designed to identify antigen-specific T-cells; MHC multimers can bind directly to T-cell receptors of a particular specificity, and this specificity is determined by the combination of the MHC molecule and peptide presented on it. Similarly, we used RNA electroporation to modify the function of T-cells, introducing antisense oligonucleotides (ASOs) targeting various exons of undesired genes.

To assess the possibility to deliver ASOs in activated primary T-cells, we used a scrambled-ASO tagged with FAM and we introduced it in the T-cells alone or in combination with the mRNA coding for a TCR and looked for their presence using flow cytometry. As shown in the central panel of FIG. 1, 94% of the T-cells electroporated with the FAM-tagged ASO alone are positive for the fluorophore, indicating that the electroporation is an effective way to deliver the oligomers. Similarly, the panel on the right shows that T-cells that are electroporated with the TCR together with the FAM-ASO are positive for both the transfectants. Most importantly, again 94% of the T-cells show positivity for the ASO, meaning that the introduction of two different molecules does not reduce the efficiency in the delivery. The right plot of FIG. 1 shows also that the double-electroporated T-cell are double-stained with the two fluorophores used in the assay, that means that we are able to deliver both the transfectants in a single reaction and consequently we could be able to modify the T-cell specificity (with the introduction of a TCR) and the T-cell function (with the introduction of an ASO).

Moreover, in a different experiment, we electroporated the TCR and the ASO in the same T-cells, in two separate reactions 16 hours apart from each other. We were interested in this different schedule because the peak of the expression of the TCR and the peak of activity of the ASOs could not coincide and the simultaneous delivery of them could lead to a not coordinated effect on the T-cells. Also with this particular experimental schedule, we managed to get both the expression of the TCR and the delivery of the ASO (data not shown). Thus, we can prove that we are able to introduce the two molecules at different time points to let us tune their effect at their best timing.

EXAMPLE 2

Gene Expression Can Be Modulated by ASOs in Primary T Cells.

After having demonstrated the feasibility of the transfection of ASOs in primary activated T-cells (with or without HBV-specific TCR), we moved forward to test the ability of the oligonucleotides to interfere with the splicing of a target gene. For the proof of concept, we chose to design an ASO targeting the exon 2 of the interferon-γ (IFN-γ) pre-mRNA, since in the lab we can exploit various tools to assess the presence and the activity of such cytokine. We designed primers surrounding the exon 2 of (IFN-γ) in order to obtain a PCR product that amplifies both the full length and the short (exon-skipped) isoform performing a simple PCR on the cDNA of the transfected cells [11]. The control to assess the specificity of the technique is performed transfecting primary cells with a non-targeting/scrambled sequence. FIG. 2.A shows the results of the PCR: it is evident that the ASO interferes with the splicing of the pre-mRNA in a dose-dependent manner, leading to the exclusion of exon 2 from the final mRNA. When only 8% of the T-cells transfected with 500 picomoles of the IFN-γ-targeting ASO show an effect at the mRNA level, the T-cells transfected with triple amount of the same oligomer show a 92% reduction of the full-length transcript. T-cells treated with a scrambled ASO do not show any modification of the IFN-γ transcript. However, as clear in FIG. 2.A, we could not achieve the elimination of the exon-skipped mRNA via nonsense-mediated RNA decay, as we expected. After a bioinformatics search on immune-related proteins, we realized that many splice variants are normally present in physiological conditions, although often they are not functionally characterized.

We then tried to measure the abundancy of IFN-γ at the protein level, to verify that the modification of the splicing was reflected in the knock-down of the protein. FIG. 2.B shows that, despite an almost complete elimination of the full-length mRNA from the transfected cells, IFN-γ could still be detected by intracellular cytokine staining. The staining reveals only a 25% reduction of fluorescence of the IFN-γ-specific ASO treated T-cells to the T-cells transfected with the scrambled ASO.

This discrepancy between the results at mRNA and at the protein level may be explained by the presence of the exon-skipped form detected by PCR and not eliminated via NMD: this mRNA could be translated anyway into a shorter isoform of IFN-γ that is not-specifically detected by the antibody in the intracellular cytokine staining. To test for the presence of this exon-skipped isoform in the T-cells at the protein level we could perform a Western blot, but the feasibility of the assay and the quality of the results still depend on the ability of an antibody to detect not specifically the shorter protein, so we concurred that it was irrelevant to the objective of our study.

We therefore proceeded to test the function of the IFN-γ produced by the ASO-transfected cells, as a measure of the effect of the treatment. For this purpose we used a well-established functional assay that involves the use of a HuH7 cell line transfected with a plasmid that contains a HCV-replicon very sensitive to IFN-γ antiviral effect [17] (FIG. 3.A). The plasmid used for the transfection contains also luciferase as a reporter-gene, therefore the luciferase activity detected in the cells is proportional to the "replication" of HCV (FIG. 3.A).

We cultured overnight the HCV-replicon cell line in the presence of the supernatant derived from the stimulation of the ASO-treated T-cells and we performed a luciferase assay to verify whether the IFN-γ produced was able to stop the production of replicons. FIG. 3.B shows that stimulated T-cells that have been transfected with the ASO targeting IFN-γ are less competent in the control of the viral replication (50% less compared to T-cells electroporated with a scrambled ASO). This demonstrates that the cytokine derived from the exon-skipped isoform is not functional.

Lastly, since one of the main goals of the method of transfection used is the transiency of the effect, we checked for how long the exon skipping was maintained at the mRNA level. In FIG. 4 we see that the effect of the treatment is diluted with time and is totally disappeared 96 hours after the electroporation.

EXAMPLE 3

Cytotoxicity Can Be Modulated by ASOs in Primary T Cells.

As mentioned in the introduction, one possible drawback of the use of adoptive T-cell transfer for the therapy of malignancies like HCC, is the hepatic cytotoxicity, as virtually all the liver could be target of the effector T-cells, leading to serious consequences. One measure adopted to limit this risk and improve the safety of the therapy is the transiency of expression of the T-cell receptor induced by the electroporation, but we asked if we could also be able to modify the cytotoxic function of the TCR-redirected T-cells using the antisense technology. Using the same set up, we introduced ASOs targeting exon 3 and exon 2 of the pre-mRNA of granzyme B (ASOs #266 and #267) and perforin (ASOs #268 and #269), respectively. Perforin and granzyme are the two main effectors playing in cell-cell cytotoxicity.

In FIG. 5 we show that we can detect a modification of the splicing of the two proteins 24 hours after the electroporation at the mRNA level (and already 6 hours after the treatment, data not shown). Granzyme-specific ASOs can produce 91% of exon skip (#266) and 70% of exon skip (#267), compared to the scrambled ASO. Interestingly, we can notice that granzyme B is naturally presenting three different splicing isoforms, and the ASOs are only modifying the proportions between full length and short length transcripts. Unfortunately in the literature there's no report of the presence at the protein level and of the physiological function (if any) of these different isoforms. Consequently, we do not know whether these isoforms are translated into proteins and whether they are also detected by the antibodies we use for detection in the intracellular cytokine staining.

In addition, from the same figure we notice that the full-length band of the mRNA of perforin is not detectable after the transfection of the perforin-specific ASO, but at the same we are unable to detect also the shorter isoform that we are supposed to obtain after the treatment. The absence of the full-length transcript could be explained by the effect of the ASOs targeting the pre-mRNA of perforin. On the other hand, the exon-skipped transcript produced by the splicing alteration could be subjected to nonsense mediated RNA decay and this may explain the absence of the band from the gel. However, to verify this hypothesis more experiments need to be carried on.

Next, we moved on to check whether the modification at the RNA level was reflected into some modification of the protein expression, so we performed an intracellular cytokine staining to measure the levels of the two target proteins. FIG. 6 shows the percentage of granzyme and/or perforin positive cells and the median fluorescence intensity (MFI), as a measure of the abundance of the proteins in the cells 24 hours after the electroporation. From FIG. 6 we do not detect much modification in the levels of granzyme B. This could be explained by the existence of the multiple isoforms above described. Those transcripts could in fact be translated into shorter proteins and be bound by the antibody used in the assay. To verify this hypothesis, as for the intracellular cytokine staining for IFN-γ in the previous paragraph, a Western blot is needed to assess the presence of these shorter proteins in the T-cells, but the same limitations are met.

On the other hand, the perforin-positive T-cells treated with the specific ASO show a lower MFI compared to the T-cells electroporated with the scrambled ASO (even if the reduction is not dramatic, only 80%). Interestingly, we see a consistent and substantial drop in the count of perforin positive cells (60% compared to T-cells treated with a scrambled ASO). A possible explanation for this phenomenon is the fact that the ASO targeting the perforin pre-mRNA is very efficacious and, once entered in the cell, it is able to fully stop the production of the protein. For this reason the count of positive cells dropped, while the MFI did not change dramatically.

The assay shows also that the effect of the ASO is specific, as T-cells treated with an ASO targeting perforin do not show any modification in the levels of granzyme B.

We then moved forward to verify whether the cytotoxic ability of ASO-treated T-cells was modified due to the exon skip induced by the antisense oligonucleotides. Therefore we set up a cytotoxicity assay using xCELLigence® RTCA DP (Acea Biosciences). xCELLigence® RTCA DP is an instrument that uses non-invasive electrical impedance to monitor cell proliferation and attachment in a label-free, real-time manner [18]. The functional unit of the assay is a set of electrodes on the bottom of a plate well. When in a conductive solution, the application of an electric potential across the electrodes causes electrons to exit the negative terminal and deposit onto the positive terminal, passing through the conductive medium (FIG. 7A). This phenomenon is dependent upon the direct interaction between the electrodes and the solution, so the presence of adherent cells at the electrode-solution interface impedes electron flow. The magnitude of the impedance is dependent on the number, the size and shape of the cells, and it is possible to obtain a measure of these variables (Cell Index) exploiting the impedance measured in the bottom of the wells (FIG. 7B). Using this experimental method, we were able to set up a co-culture of HBV-specific TCR-redirected T-cells and HBV producing cells to study the killing ability of our modified effectors.

FIG. 8.A shows the ability of HBV-specific T-cells to kill HBV-producing cells. It is evident that the impaired production of perforin and/or granzyme B in the ASO knocked-down T-cells prevents them from killing their targets as the scrambled ASO-transfected TCR-redirected T-cells. More in detail, we see that, 24 hours after the addition of effectors in the culture, scrambled-ASO treated TCR-redirected T-cells killed almost all the adherent cells, causing a drop in the Cell Index, as the targets detached from the bottom of the well (red). The same phenomenon is observed in the wells were HBV producing cells were cultured together with granzyme knocked-down T-cells (yellow). Conversely, HBV-specific T-cells treated with a perforin-specific ASO show 20% of reduction in their killing ability 24 hours after the beginning of the co-culture (blue). Interestingly, when TCR-redirected T-cells are transfected with ASOs targeting perforin and granzyme B transcripts together, their cytotoxic ability decreases even more (up to 35%). The result shows that the effect of the two transfectants was additive (green), even if we saw no change when the T-cells were granzyme B knocked-down. This discrepancy could be simply explained considering the biology of the system we were trying to disrupt. In physiological conditions in fact perforin is used by cytotoxic lymphocytes (CTLs) as a pore forming cytolytic protein. The pores formed in the membrane of the target cells allow for the passive diffusion of granzyme B, which is pro-apoptotic protease that cleaves caspases involved in the process of programmed cell death. As a consequence, the knock-down of granzyme B alone will not modify dramatically the cytotoxic ability of the CTLs, as the action of perforin alone is sufficient to induce lysis of the target cells. On the other hand, when both the proteins are knocked-down, the pro-apoptotic pathway and the cytolytic pathway are both disrupted and the killing ability of the CTL is substantially modified.

FURTHER EXAMPLES AND DATA

FIG. 9 shows that, typically, AONs do not affect the viability of transfected T cells and do not interfere with TCR expression. FIG. 9(*a*) shows the viability of T cells EP with HBV-specific TCR, with AONs or both, compared to non electroporated cells. FIG. 9(*b*) shows TCR expression in activated or resting T cells EP with TCR or TCR+AON (measured with MHC-multimer staining in flow cytometry).

FIG. 10 also shows that, typically, AONs do not affect antiviral activity and cytotoxicity of transfected TCR-redirected T cells. FIG. 10(*a*) shows a flow cytometry with intracellular cytokine staining; and FIG. 10(*b*) shows results obtained from an impedance cytotoxicity assay. It can be seen from the figures that HBV specific TCR-redirected T cells transfected with a scrambled AON show comparable inflammatory cytokines production (A) and cytotoxicity (compared to the not treated TCR-redirected T cells) when in culture with HBV-expressing targets.

Figure 11A:
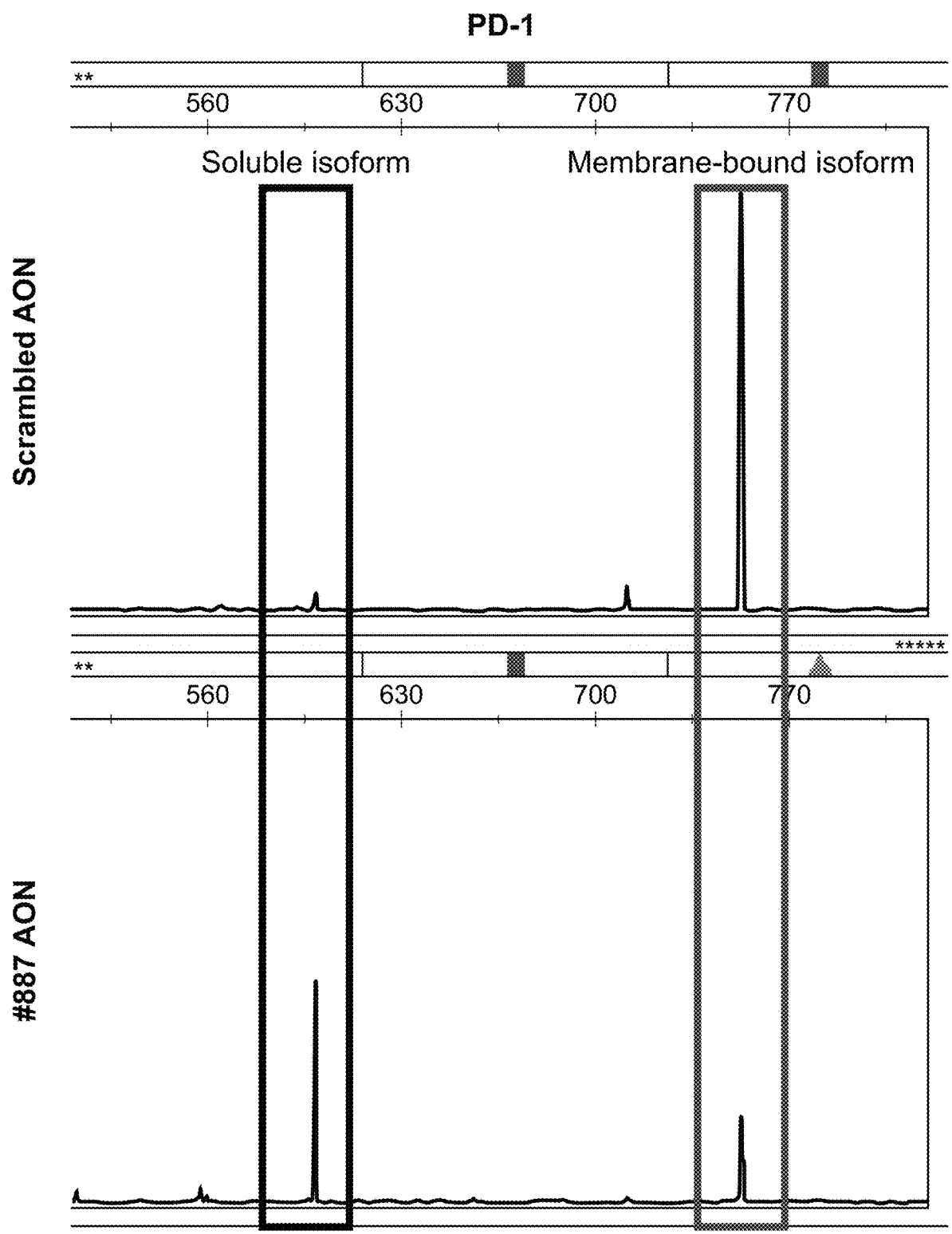
Figure 11B:
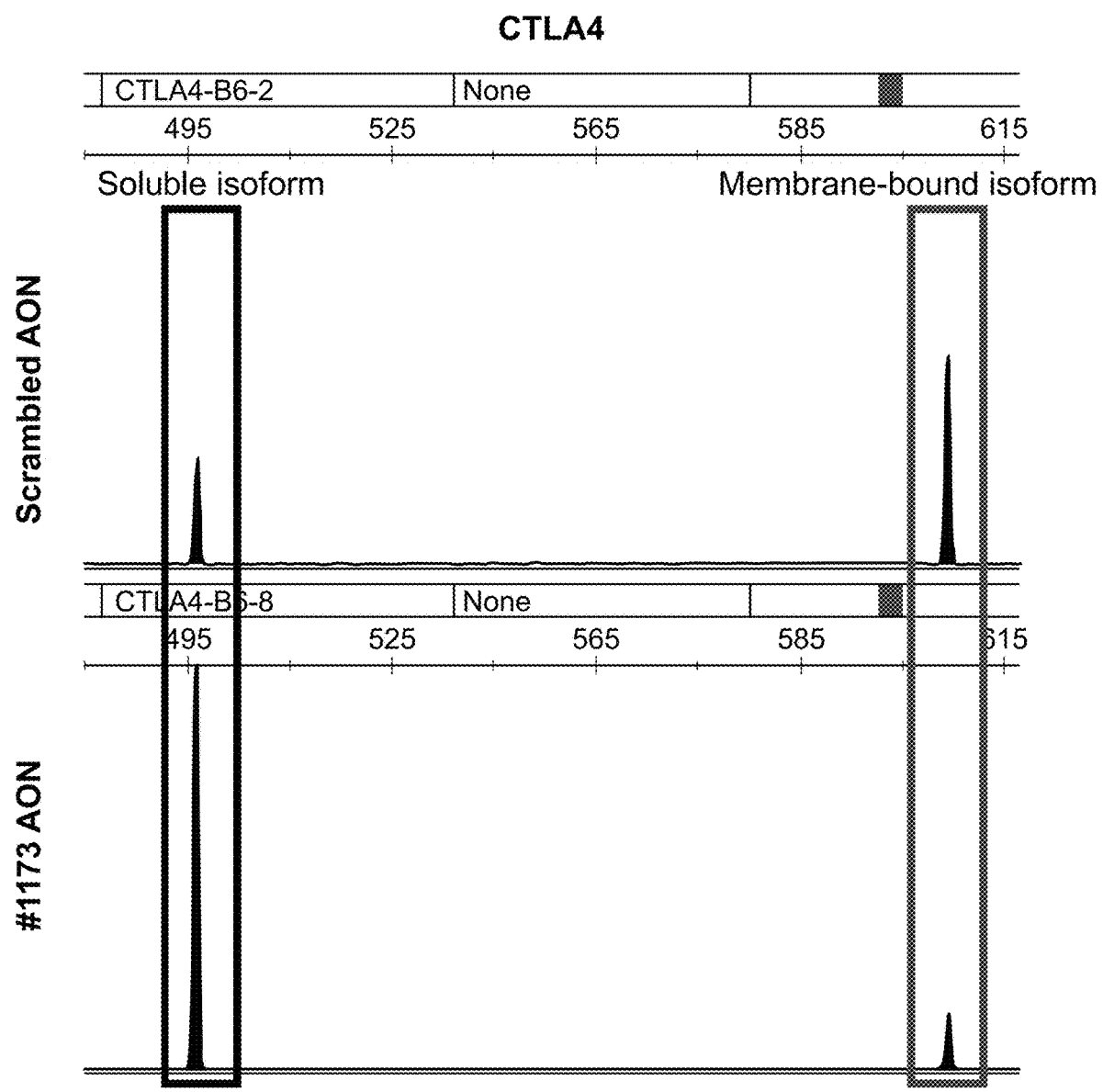
Figure 12A:
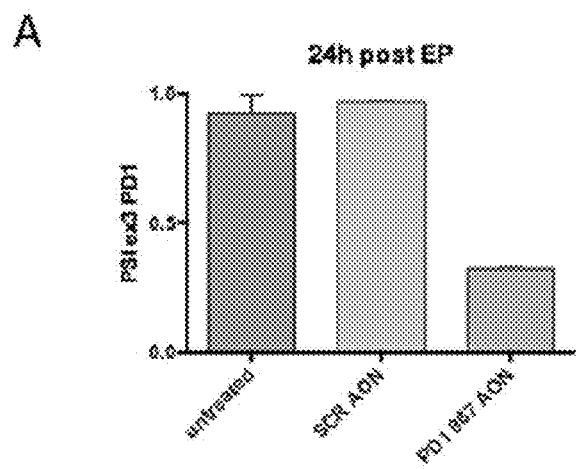
Figure 12B:
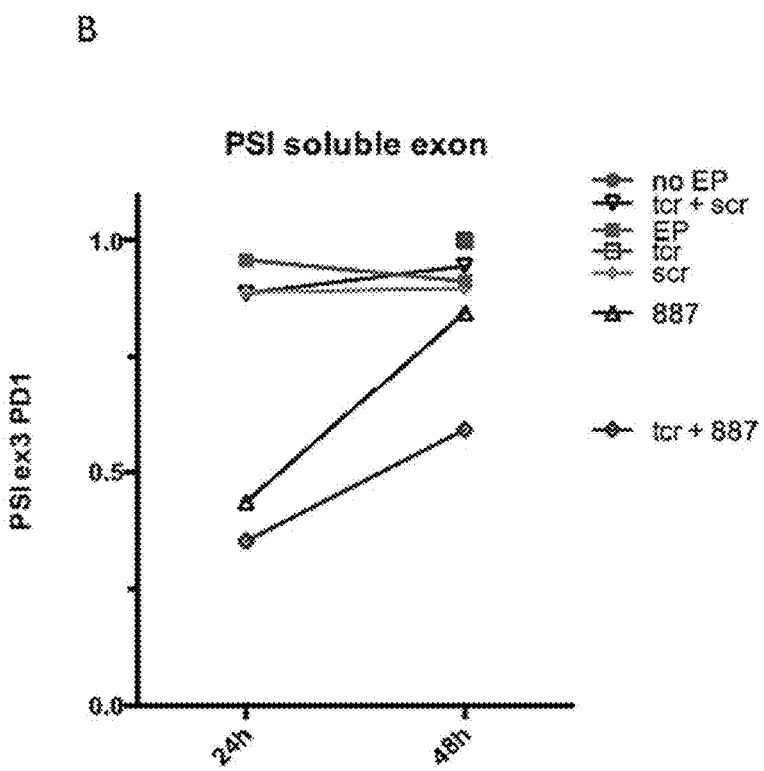
Figure 12C:
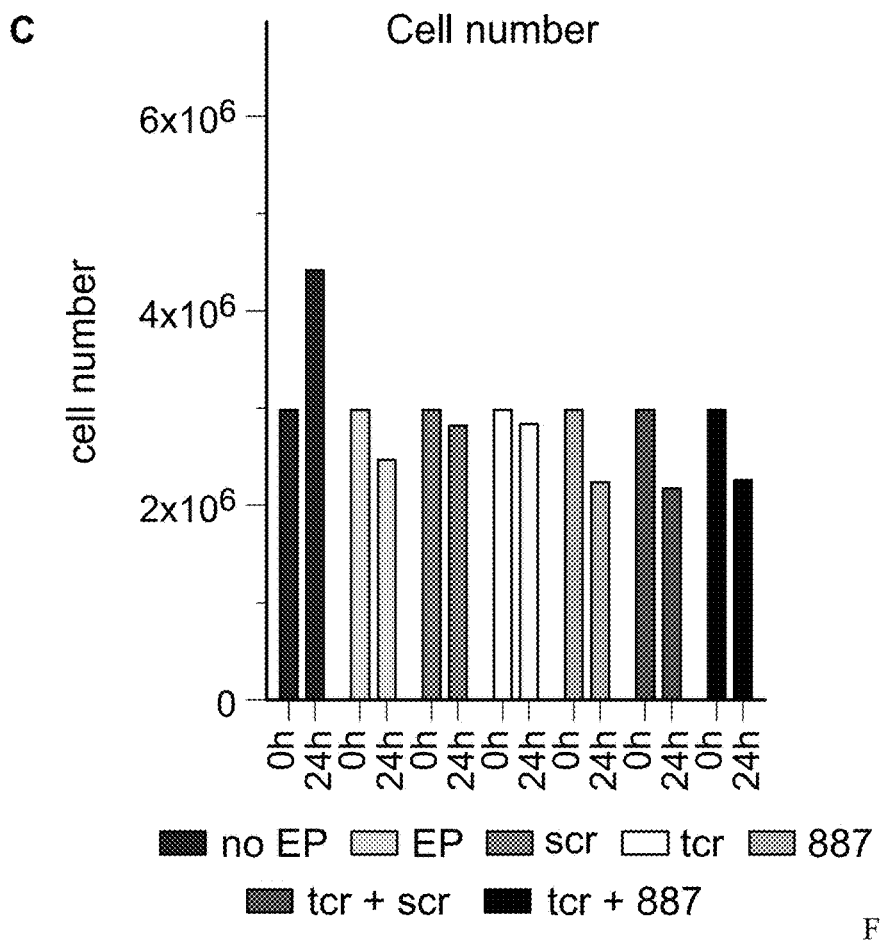
Figure 12D:
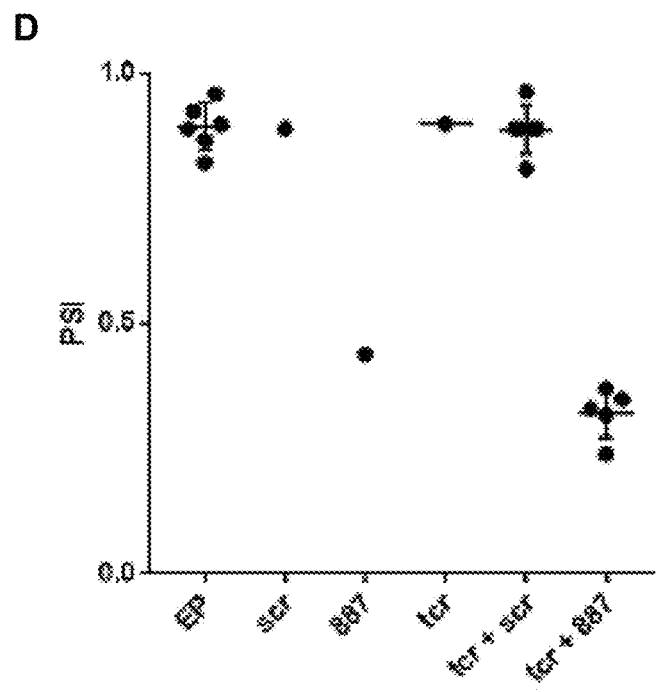

In the present invention, however, the inventors have found that AONs of the present invention can alter the function of a T cell, in particular, those sequences identified in the present application. For example, AONs of the present invention can be efficiently electroporated in primary human T cells and they are able to alter splicing selectively. With reference to FIG. 11, AON #887 (SEQ ID NO. 6508) and #1173 (SEQ ID NO. 2565), at 24h post-electroporation, show a switch from membrane-bound to soluble PD-1 and CTLA4 respectively. Images show the Fragment Length Analysis PCR on T cells cDNA. The height of each peak is proportional to the transcript abundance.

AONs of the present invention are also able to specifically switch exon inclusion without altering cell viability and their effect is compatible with simultaneous TCR electroporation. With reference of FIG. 12, AON #887 (SEQ ID NO. 6508) shows a switch from membrane-bound isoform to soluble isoform of PD-1 for 24/48h post-electroporation at mRNA level (A and B). Cell viability at 24 h post-electroporation is not affected significantly, also in concomitant electroporation of the TCR mRNA (C). Multiple electroporation of AON alone or AON+TCR show a consistent decrease in PSI of PD-1 exon 3 (D).

Figure 13A:
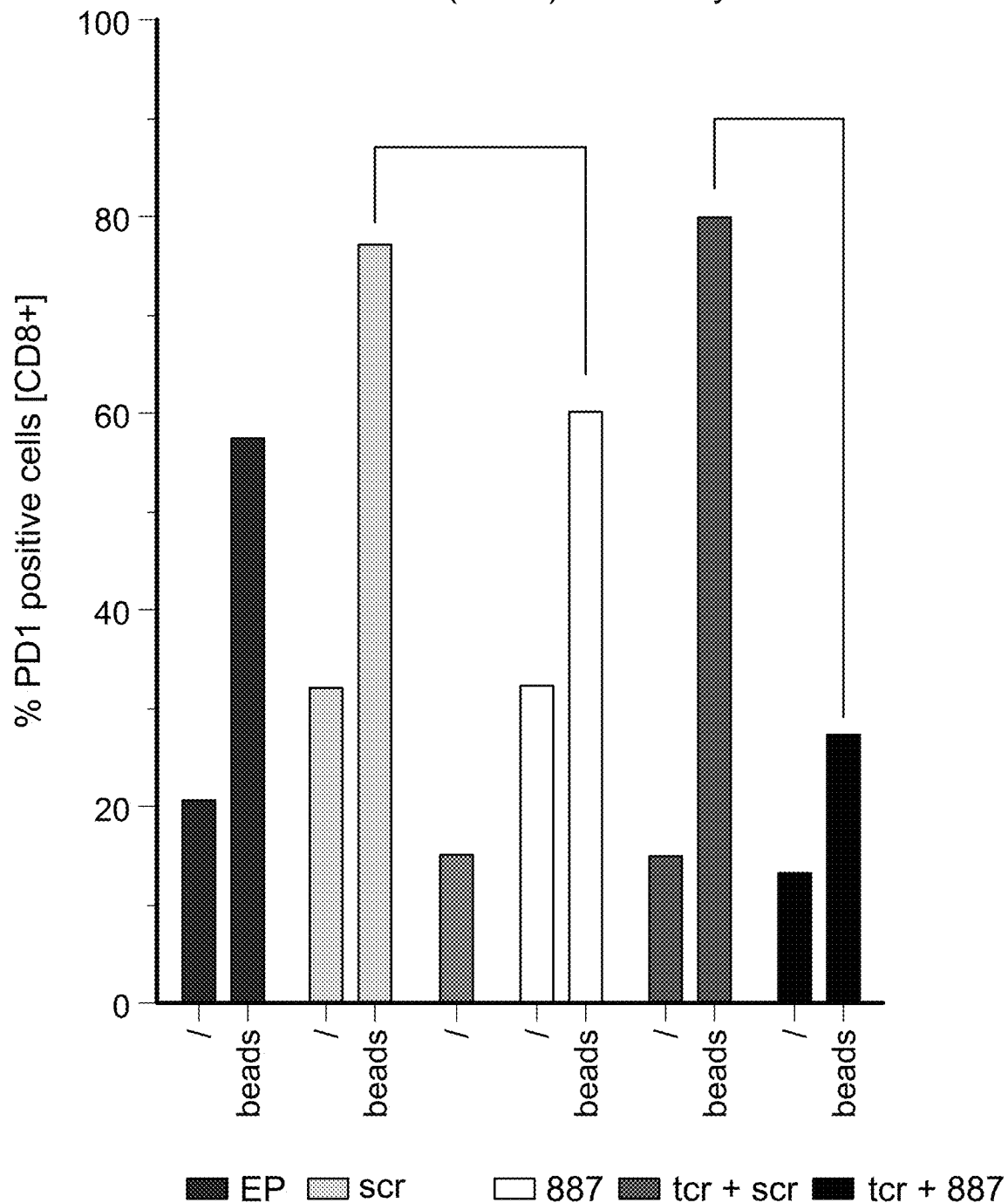
Figure 13B:
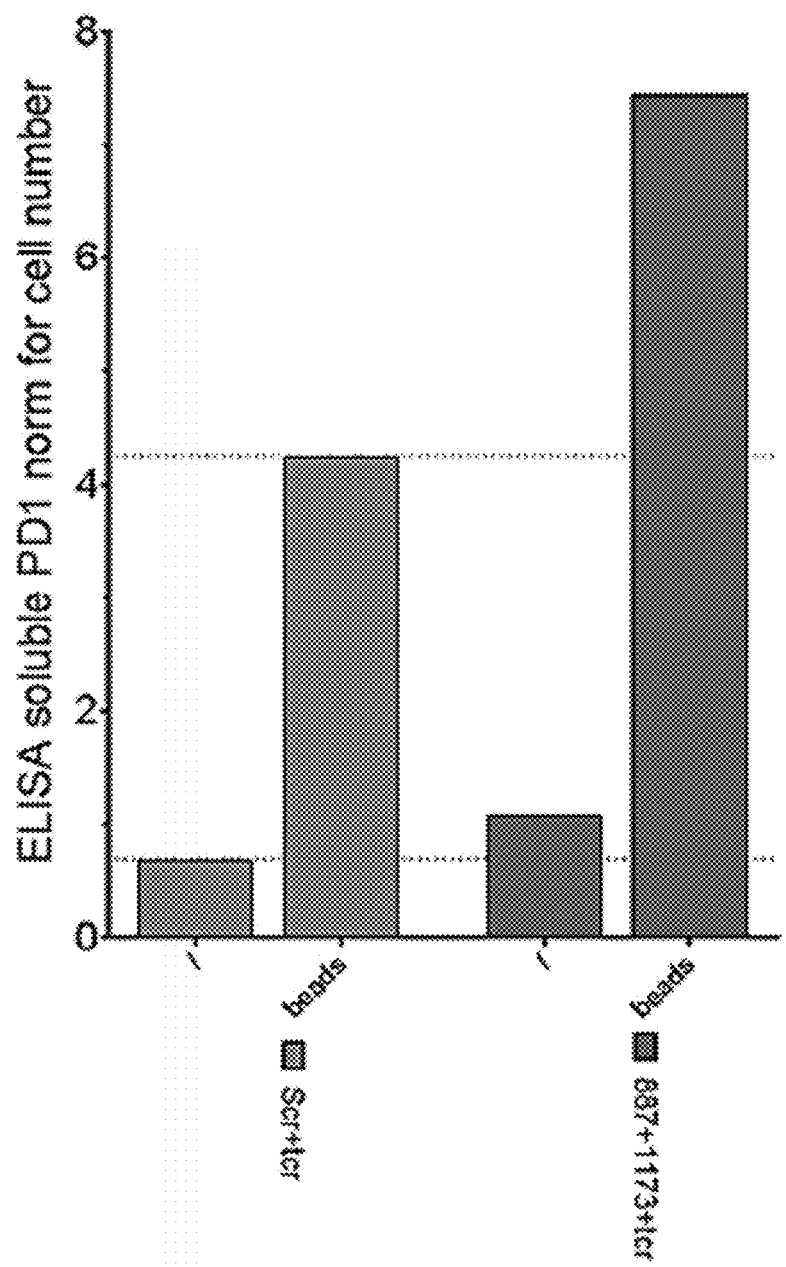
Figure 13C:
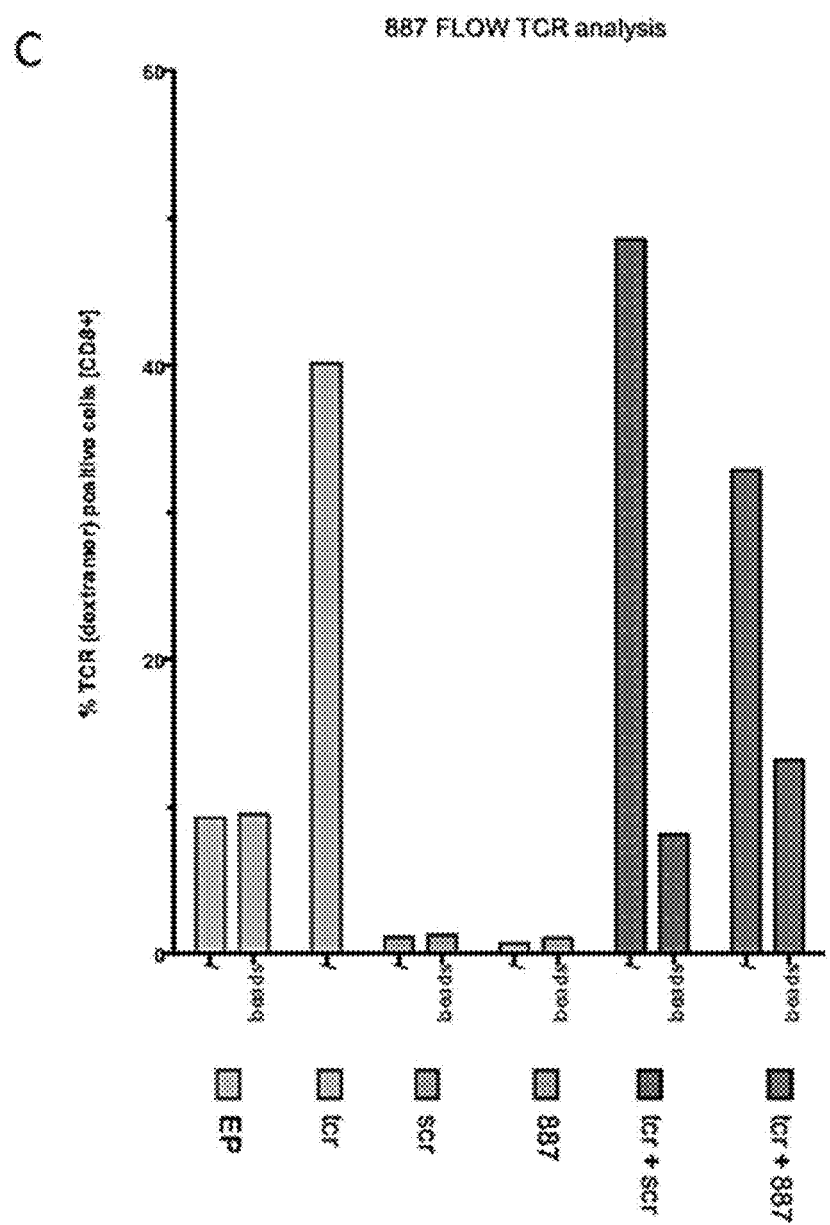

In addition, AONs are able to specifically reduce the membrane-bound proteins without affecting TCR expression. With reference to FIG. 13, AON #887-electroporated T cells show a switch from membrane-bound isoform (A, flow cytometry) to soluble isoform of PD-1 (B, ELISA) at the protein level. Flow cytometry data of the electroporated TCR are not altered significantly by the AON (C).

Figure 14A:
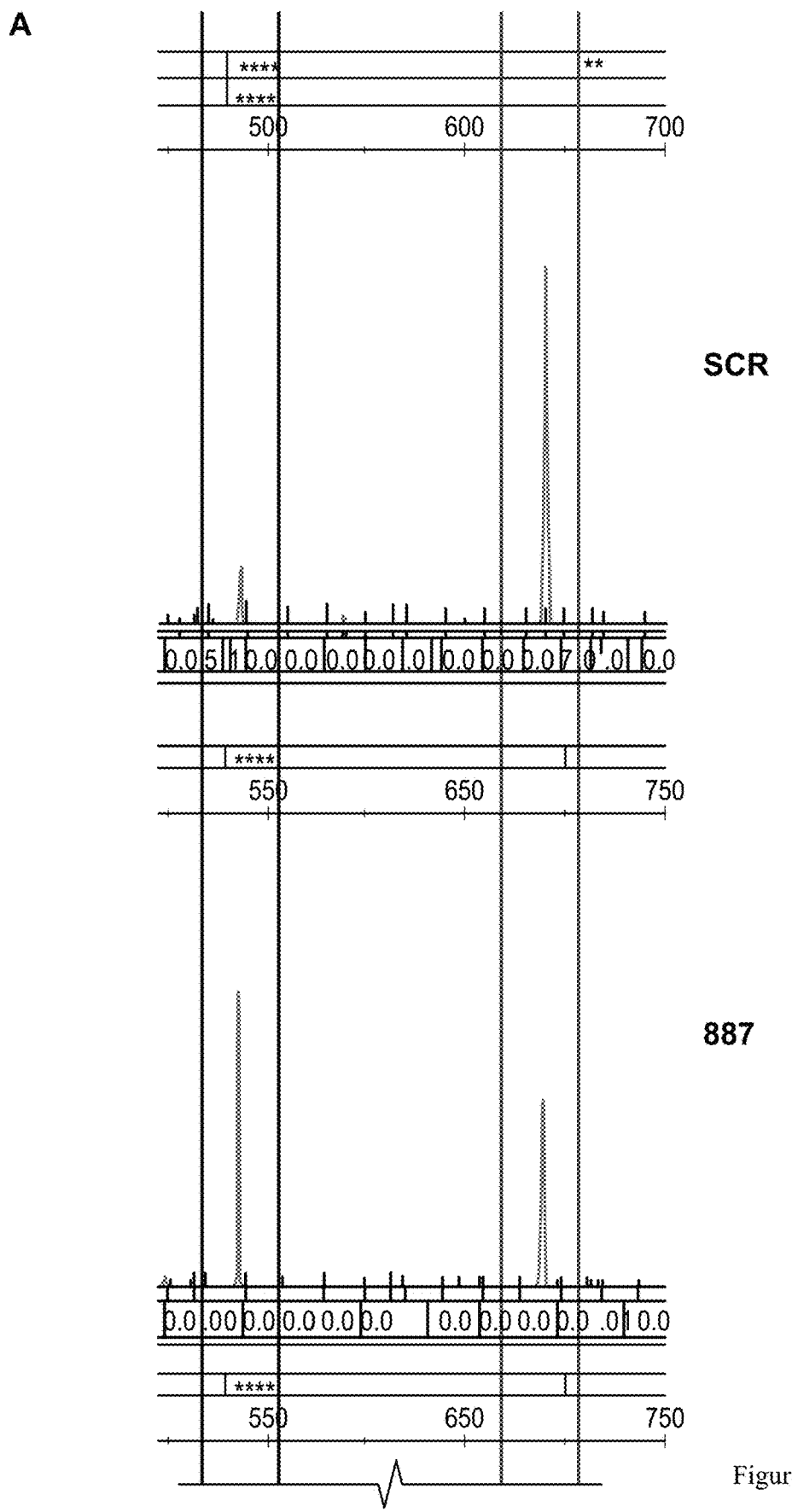
Figure 14A:
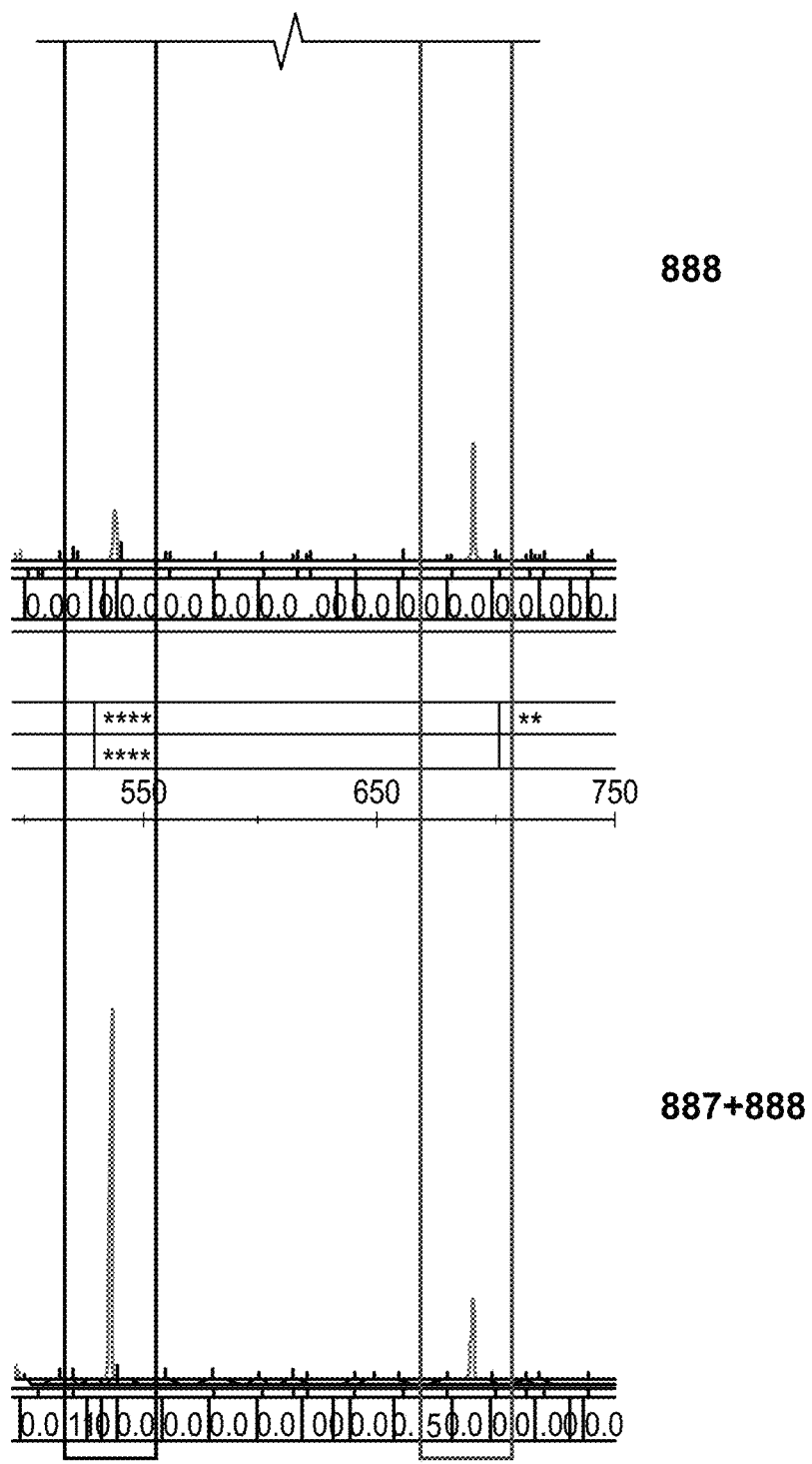
Figures 14B, 14C:
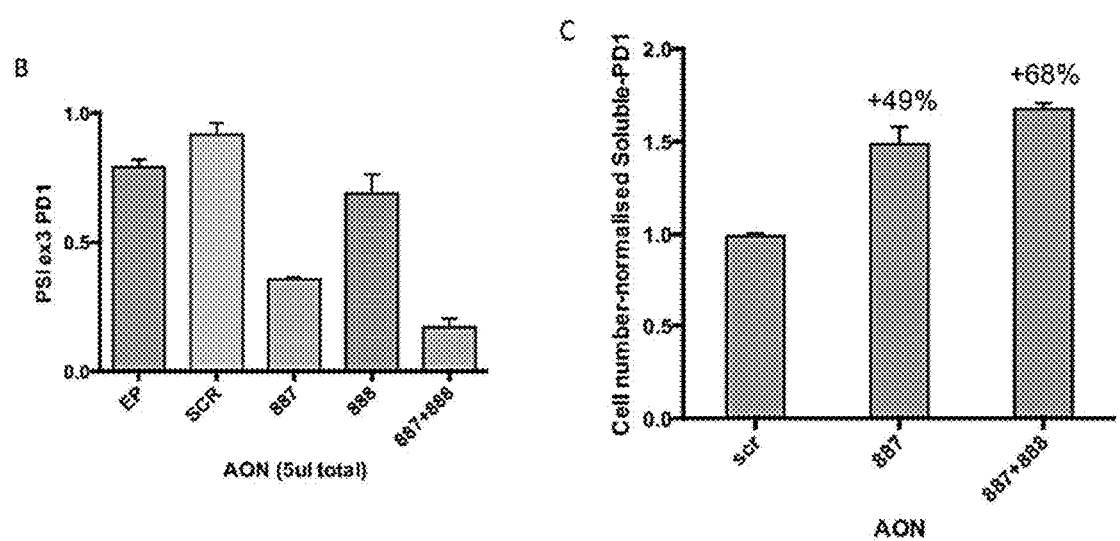

A combination of AONs May also be able to specifically reduce the membrane-bound PD-1 more than AONs in single-use. With reference to FIG. 14, AON #887+#888-electroporated T cells show a switch from membrane-bound isoform (highlighted in the box on the right (A)) to soluble isoform of PD-1 (highlighted in the box on the left, (A)) at the mRNA level. The quantification of the exon 3 PSI of PD-1 is shown in (B). The increase in soluble PD-1 is reflected at the protein level with an increased ELISA score (C).

Figure 15:
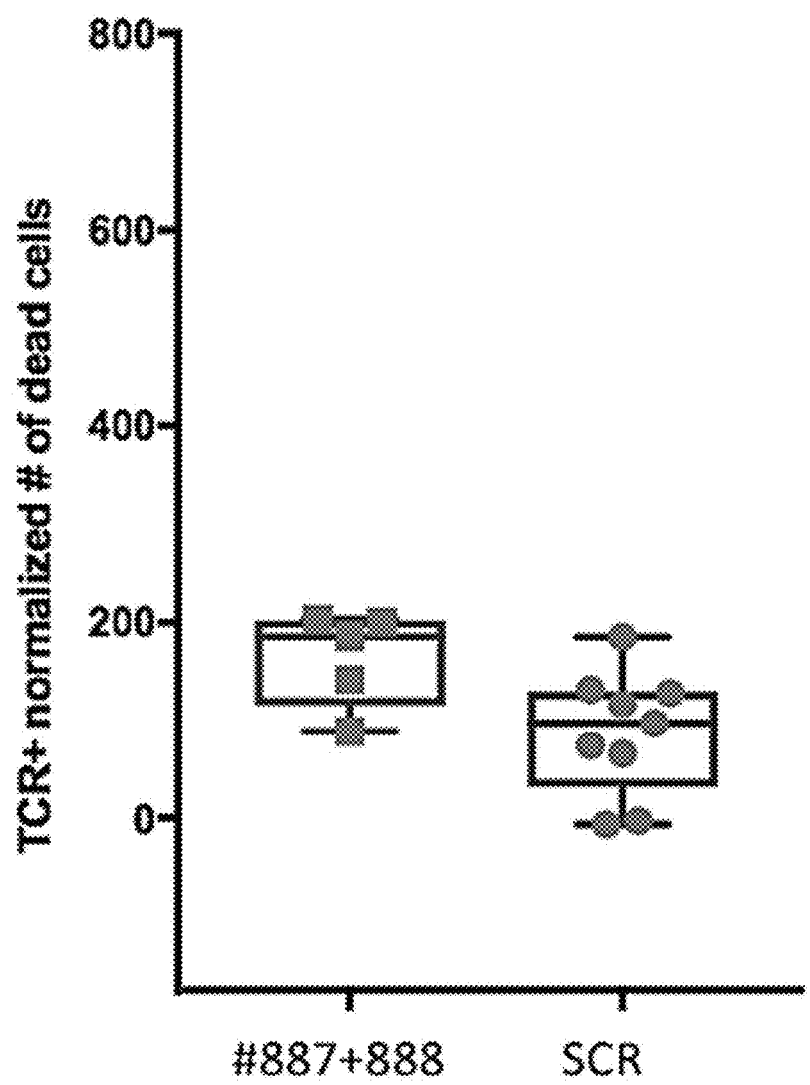

Specifically, AON #887+#888 (SEQ ID NO. 69648) are able to enhance T-cell mediated killing of target cells. FIG. 15 illustrations how AON #887/888+TCR-electroporated T cells show an overall killing increase of HBV hepatocellular carcinoma's in a 3D model compared to AON SCR+TCR-electroporated cells.

FIGS. 16 and 17 illustrates the effect of the present AONs on the target IFN-γ. The exon skipping induced by an IFN-γ-specific AON is dose dependent and transient. FIG. 16 shows 1.5/2.5/5 femtomoles of AON per cell with PCR done on RNA extracted at 0-6 12 18 24 48 72 hours after transfection with different amounts of an AON targeting IFN-γ.

Figure 17A:
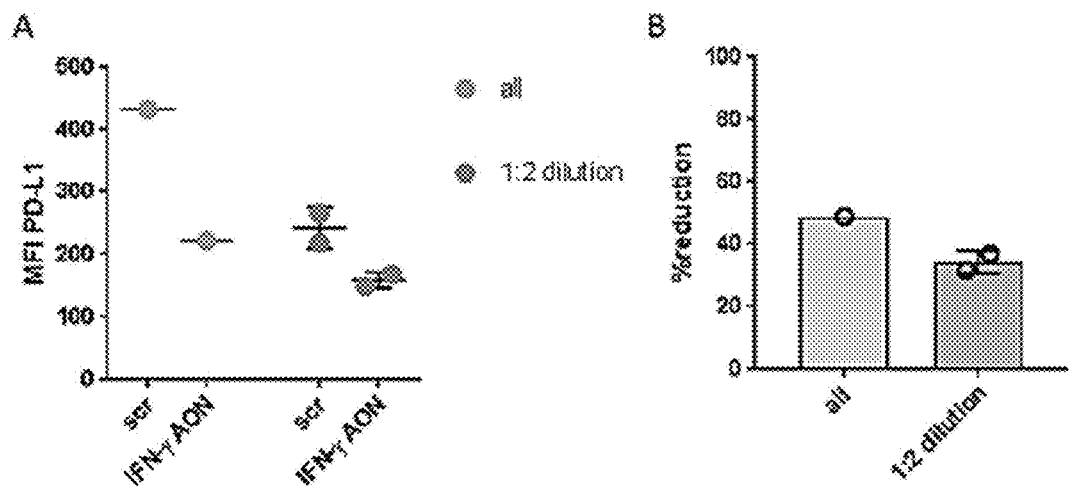
Figure 17B:
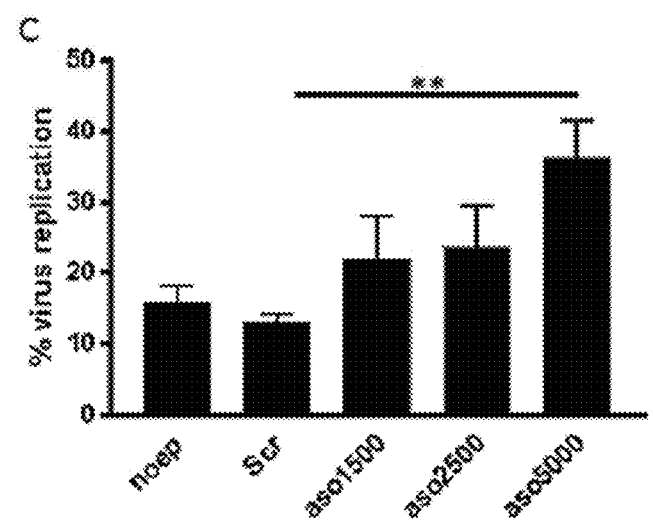

FIG. 17 illustrates the functional change of T cells treated with an AON targeting IFN-γ. It was assumed that T cells that produce less IFN-γ will induce less PD-L1 expression in the TME. FIG. 17(a) illustrates how HBV-specific TCR-redirected T cell (with and without an AON targeting IFN-γ) are cultured with HBV-expressing targets and the supernatant is collected after 5 hours. Subsequently, the supernatant is added on THP-1 cells (alone or diluted) and the expression of PD-L1 on THP-1 is measured by flow cytometry. FIG. 17(a): PD-L1 MFI on THP-1. FIG. 17(b): percentage reduction of PD-L1 in the THP-1 cultured with supernatants from AON-treated TCR-redirected T cells (compared to scrambled control). FIG. 17(c): viral replication (measured with luciferase assay) in JFH cells after culture with supernatants of activated T cells transfected with IFN-γ AON. Here, JFH-luciferase HCV replicons are a cell line that express HCV linked to luciferase. This cell line is very sensitive to IFN-γ antiviral activity. The supernatants from T cells treated with that AON are less able to control viral replication in JFH cells, hence they produce less IFN-γ.

Figures 18A, 18B:
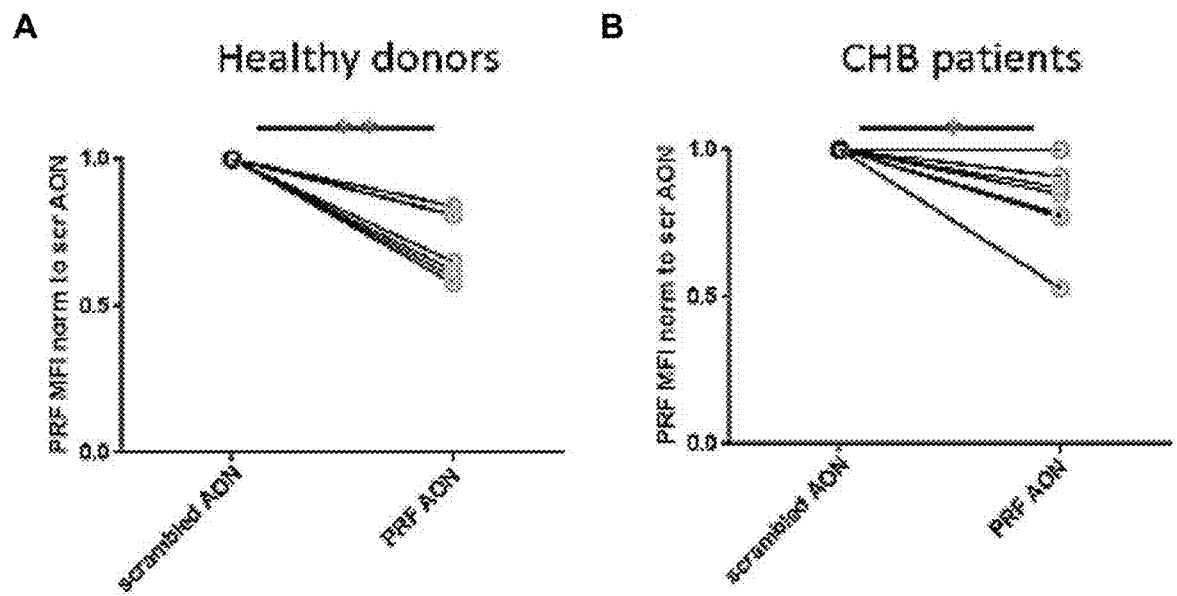
Figures 18C, 18D:
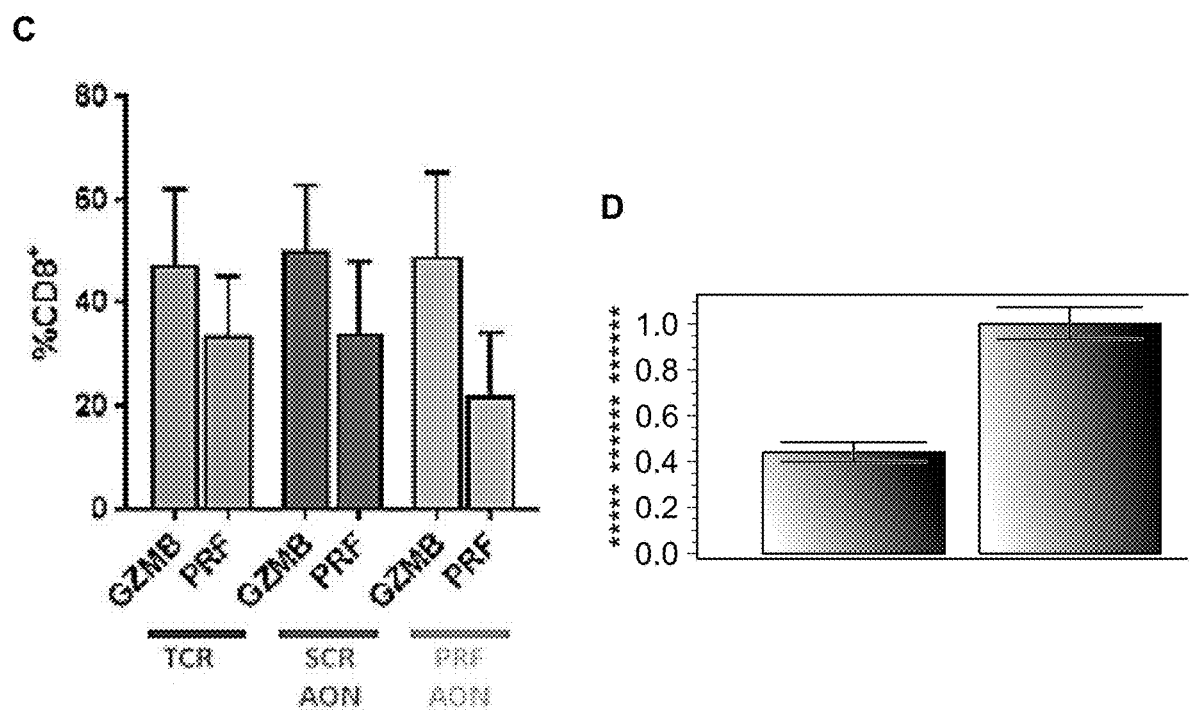

FIG. 18 illustrates an AON targeting PRF specifically reduces the protein levels and can be used in T cells from healthy donors or CHB patients. In FIGS. 18(a) and (b), intracellular cytokine staining (PRF) of T cells treated with an AON targeting PRF expanded from healthy donors or Chronic Hepatitis B patients. The experiment shows that the phenotype is achieved also in the T cells of interest. FIG. 18(c) shows the ICS of PRF and GZMB of TCR-redirected T cells (grey), T cells treated with an scrambled AON (middle 2 bars) and T cells treated with an AON targeting PRF (right most 2 bars). The levels of GZMB are not modified by the AONs, while the levels of PRF are modified only in T cells treated with the PRF AON. FIG. 18(d) shows qPCR on PRF mRNA. The levels of PRF mRNA are reduced after transfection of the specific AON of the present invention.

Figures 19A, 19B:
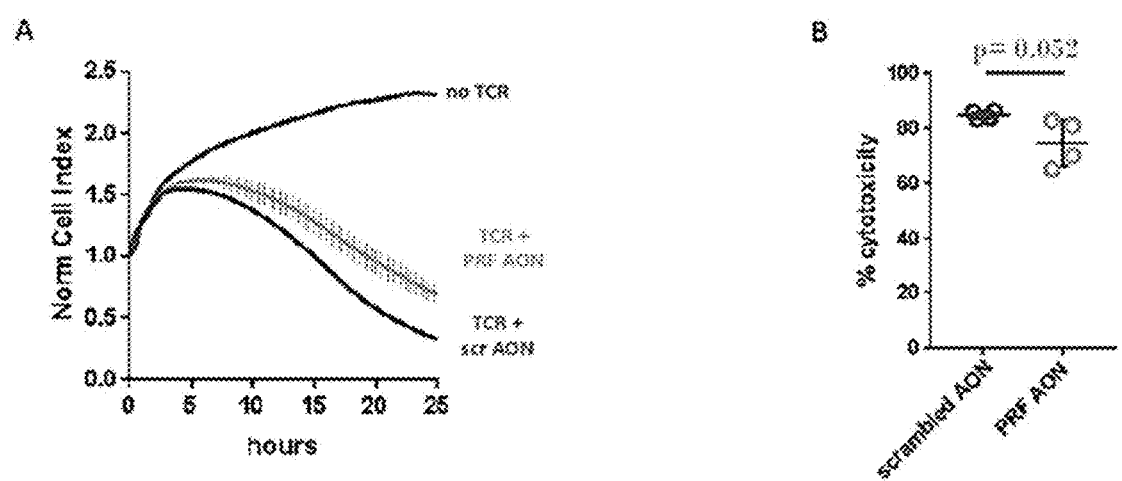

FIG. 19 illustrates TCR-redirected T cells treated with an AON targeting PRF are less cytotoxic. FIG. 19(a) is a representative graph obtained in a cytotoxicity assay in which HBV-specific TCR-redirected T cells (with and without a PRF-specific AON) are cultured with HBV-expressing targets. T cells treated with the PRF AON are less cytotoxic compared to the control. FIG. 19(b) are results obtained based on an average of experiments performed using cells from 4 different donors.

FIG. 20 illustrates the present AONs that induce the skipping of specific exons are triggering a NMD-mediated decrease of the target mRNA, particularly for targets CD244 (leftmost 2 bars), TIM3 (middle 2 bars) and TGIT (rightmost 2 bars). RT-qPCR data obtained on T cells electroporated with AON #524 (directed against CD244), #527 (vs TIM3) and #526 (vs TGIT) show that the relative abundance of mRNA of these genes is strongly decreased in presence of the respective AON.

FIG. 21 illustrates the present AONs that induce the skipping of specific exons are triggering a NMD-mediated decrease of the target mRNA, particularly for targets PRDM1 (leftmost 4 bars) and REL (rightmost 4 bars). With reference to the figure, RT-qPCR data obtained on T cells electroporated with AON #442, #443 and #444 (directed against PRDM1), #462, #463, #464 (vs REL) show that the relative abundance of mRNA of these genes is decreased in presence of the respective AON.

Figure 22A:
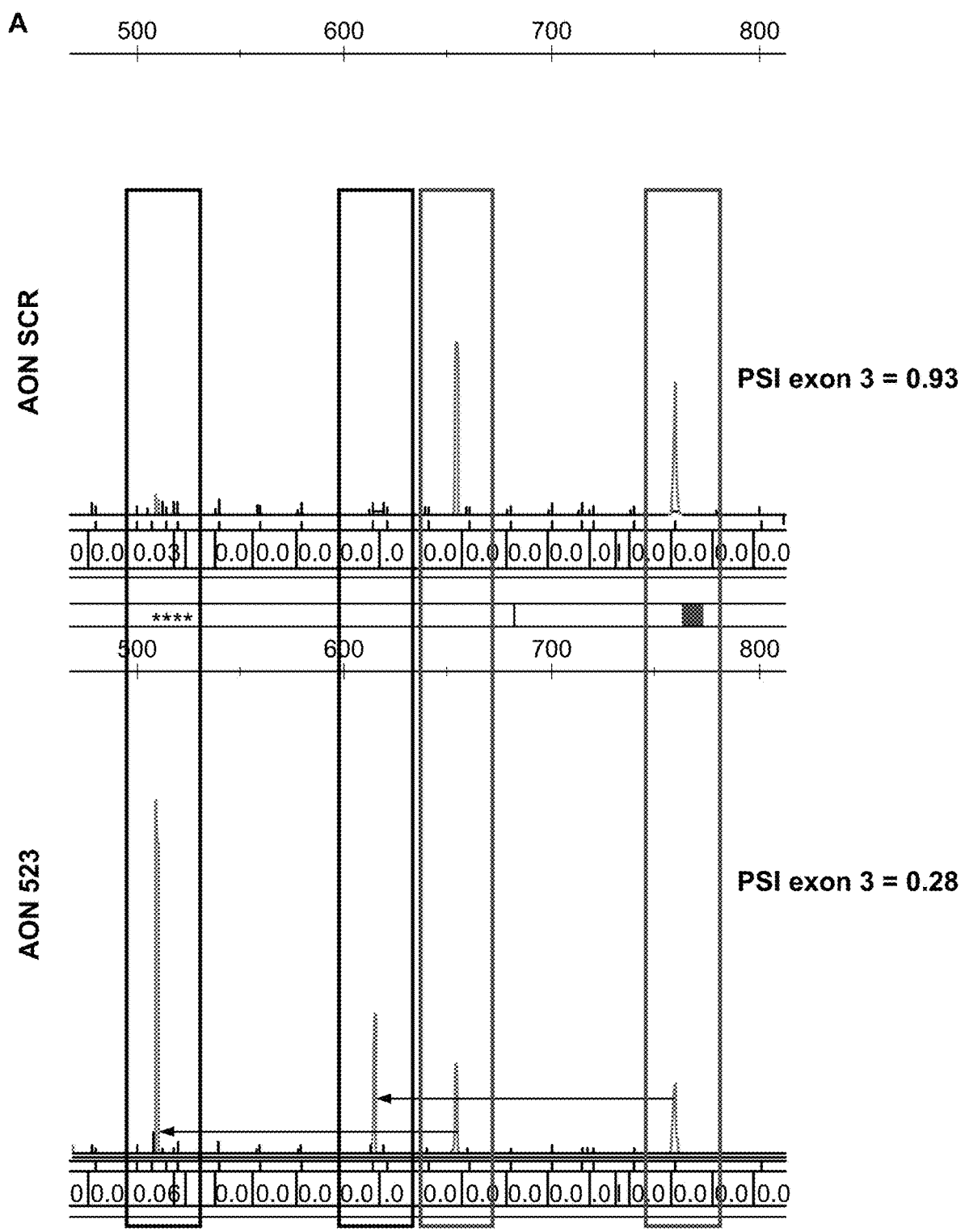
Figure 22B:
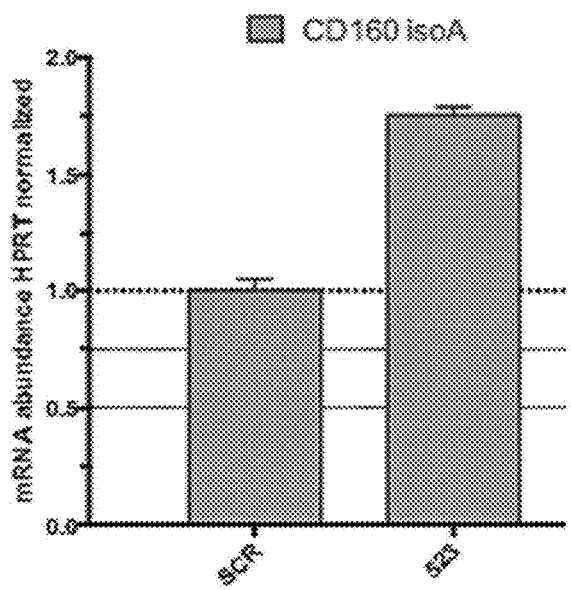

FIG. 22 illustrates how AON #523 is efficiently inducing the skipping of CD160 exon 3, causing an isoform switch. FIG. 22(a) shows FLA-PCR of T cells electroporated with AON Scramble or AON #523 show a switch from the two wild type isoforms (in green rectangles) to the isoforms excluding exon 3 (in the leftmost 2 boxes). FIG. 22(b) shows RT-qPCR data obtained on T cells electroporated with AON 523 show that the relative abundance of CD160 transcript increases.

Figure 23B:
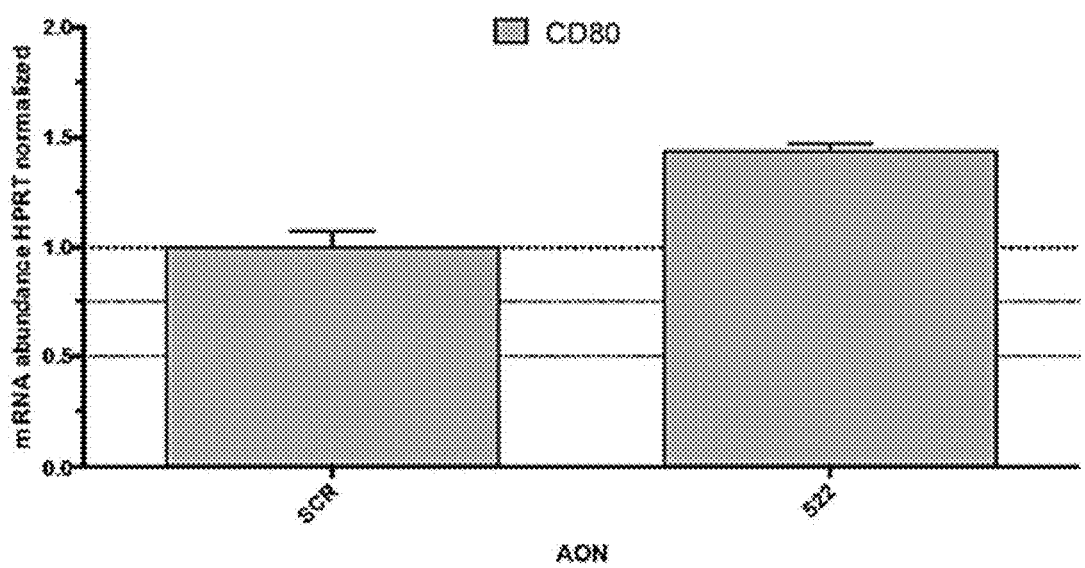

FIG. 23 illustrates how AON #522 is efficiently inducing the skipping of CD80 exon 2, causing an isoform switch. FIG. 23(a) shows FLA-PCR of T cells electroporated with AON Scramble or AON 522 show a switch from the wild type isoform (in leftmost box) to the isoform excluding exon 2 (in rightmost box), peaks. The other peaks are shown as ladder. FIG. 23(b) shows RT-qPCR data obtained on T cells electroporated with AON 522 show that the relative abundance of CD80 transcript increases.

Whilst there has been described in the foregoing description preferred embodiments of the present invention, it will be understood by those skilled in the technology concerned that many variations or modifications in details of design or construction may be made without departing from the present invention.

REFERENCES

[1] Jennifer Couzin-Frankel, "Cancer Immunotherapy," *Science* (80-.)., vol. 342, no. December, p. 1432, 2013.

[2] K. C. M. Straathof, C. M. Bollard, U. Popat, M. H. Huls, T. Lopez, M. C. Morriss, M. V Gresik, A. P. Gee, H. V Russell, M. K. Brenner, C. M. Rooney, and H. E. Heslop, "Treatment of nasopharyngeal carcinoma with Epstein-Barr virus - specific T lymphocytes," *Therapy*, vol. 105, no. 5, pp. 1898-1904, 2005.

[3] M. H. Geukes Foppen, M. Donia, I. M. Svane, and J. B. a G. Haanen, "Tumor-infiltrating lymphocytes for the treatment of metastatic cancer," *Mol. Oncol.*, vol. 9, no. 10, pp. 1918-1935, 2015.

[4] W. Qasim and A. J. Thrasher, "Progress and prospects for engineered T cell therapies," *Br. J. Haematol.*, vol. 166, no. 6, pp. 818-829, 2014.

[5] B. Savoldo, C. A. Ramos, E. Liu, M. P. Mims, M. J. Keating, G. Carrum, R. T. Kamble, C. M. Bollard, A. P. Gee, Z. Mei, H. Liu, B. Grilley, C. M. Rooney, H. E. Heslop, M. K. Brenner, and G. Dotti, "CD28 costimulation improves expansion and persistence of chimeric antigen receptor-modified T cells in lymphoma patients," *J. Clin. Invest.*, vol. 121, no. 5, pp. 1822-1826, 2011.

[6] L. a Johnson, R. a Morgan, M. E. Dudley, L. Cassard, J. C. Yang, M. S, U. S. Kammula, R. E. Royal, R. M. Sherry, J. R. Wunderlich, and C. R. Lee, "regression and targets normal tissues expressing cognate antigen Gene therapy with human and mouse T cell receptors mediates cancer regression and targets normal tissues expressing cognate antigen," *Hematology*, vol. 114, no. 3, pp. 535-547, 2009.

[7] A. J. Gehring, S. A. Xue, Z. Z. Ho, D. Teoh, C. Ruedl, A. Chia, S. Koh, S. G. Lim, M. K. Maini, H. Stauss, and A. Bertoletti, "Engineering virus-specific T cells that target HBV infected hepatocytes and hepatocellular carcinoma cell lines," *J. Hepatol.*, vol. 55, no. 1, pp. 103-110, 2011.

[8] W. Qasim, M. Brunetto, A. J. Gehring, S.-A. Xue, A. Schurich, A. Khakpoor, H. Zhan, P. Ciccorossi, K. Gilmour, D. Cavallone, F. Moriconi, F. Farzhenah, A. Mazzoni, L. Chan, E. Morris, A. Thrasher, M. K. Maini, F. Bonino, H. Stauss, and A. Bertoletti, "Immunotherapy of HCC metastases with autologous T cell receptor redirected T cells, targeting HBsAg in a liver transplant patient.," *J. Hepatol.*, vol. 62, no. 2, pp. 486-491, 2015.

[9] S. Koh, N. Shimasaki, R. Suwanarusk, Z. Z. Ho, A. Chia, N. Banu, S. W. Howland, A. S. M. Ong, A. J. Gehring, H. Stauss, L. Renia, M. Sallberg, D. Campana, and A. Bertoletti, "A practical approach to immunotherapy of hepatocellular carcinoma using T cells redirected against hepatitis B virus.," *Mol. Ther. Nucleic Acids*, vol. 2, no. August, p. e114, 2013.

[10] E. J. Wherry, S. J. Ha, S. M. Kaech, W. N. Haining, S. Sarkar, V. Kalia, S. Subramaniam, J. N. Blattman, D. L. Barber, and R. Ahmed, "Molecular Signature of CD8+ T Cell Exhaustion during Chronic Viral Infection," *Immunity*, vol. 27, no. 4, pp. 670-684, 2007.

[11] P. a. Morcos, "Achieving targeted and quantifiable alteration of mRNA splicing with Morpholino oligos," *Biochem. Biophys. Res. Commun.*, vol. 358, no. 2, pp. 521-527, 2007.

[12] G. Schmajuk, H. Sierakowska, and R. Kole, "Antisense Oligonucleotides with Different Backbones," *J. Biol. Chem.*, vol. 274, no. 31, pp. 21783-21789, 1999.

[13] E. M. McNally and E. J. Wyatt, "Welcome to the splice age: Antisense oligonucleotide-mediated exon skipping gains wider applicability," *J. Clin. Invest.*, vol. 126, no. 4, pp. 1236-1238, 2016.

[14] V. Straub, O. Veldhuizen, M. Bertoli, M. Eagle, J. Walton, G. Campion, I. Ferreira, T. Braakman, A. Labourkas, S. Giannakopoulos, T. Voit, P. Carlier, A. Moraux, L. Servais, I. De Myologie, E. Niks, J. Verschuuren, P. Spitali, and L. U. M. Cen-, "A Phase I/IIa Clinical Trial in Duchenne Muscular Dystrophy Using Systemically Delivered Morpholino Antisense Oligomer to Skip Exon 53 (SKIP-NMD)," *Hum. Gene Ther. Clin. Dev.*, vol. 26, pp. 92-95, 2015.

[15] J. T. Van Den Akker, D. Ph, B. E. Burm, D. Ph, P. F. Ekhart, M. Sc, N. Heuvelmans, T. Holling, D. Ph, A. a Janson, G. J. Platenburg, M. Sc, J. a Sipkens, M. Sc, J. M. A. Sitsen, D. Ph, A. Aartsma-rus, D. Ph, G. B. Van Ommen, D. Ph, S. J. De Kimpe, D. Ph, J. C. Van Deutekom, and D. Ph, "Systemic Administration of PRO051 in Duchenne's Muscular Dystrophy," pp. 1513-1522, 2011.

[16] N. J. Gogtay and K. Sridharan, "Therapeutic Nucleic Acids: Current clinical status.," *Br. J. Clin. Pharmacol., pp.* 1-14, 2016.

[17] J. Jo, U. Aichele, N. Kersting, R. Klein, P. Aichele, E. Bisse, A. K. Sewell, H. E. Blum, R. Bartenschlager, V. Lohmann, and R. Thimme, "Analysis of CD8+ T-Cell-Mediated Inhibition of Hepatitis C Virus Replication Using a Novel Immunological Model," *Gastroenterology*, vol. 136, no. 4, pp. 1391-1401, 2009.

[18] A. J. Davenport, M. R. Jenkins, R. S. Cross, C. S. Yong, H. M. Prince, D. S. Ritchie, J. a Trapani, M. H. Kershaw, P. K. Darcy, and P. J. Neeson, "CAR-T Cells Inflict Sequential Killing of Multiple Tumor Target Cells.," *Cancer Immunol. Res.*, vol. 3, no. 5, pp. 483-94, 2015.

SEQUENCE LISTING

The patent contains a lengthy sequence listing. A copy of the sequence listing is available in electronic form from the USPTO web site (https://seqdata.uspto.gov/?pageRequest=docDetail&DocID=US12188016B2). An electronic copy of the sequence listing will also be available from the USPTO upon request and payment of the fee set forth in 37 CFR 1.19(b)(3).

The invention claimed is:

1. An antisense oligonucleotide which modulates one or more of: T-cell ability to kill or exert a cytotoxic, anti-tumour or antiviral effect, T-cell ability to produce an anti-viral cytokine, T-cell expansion,
   wherein the antisense oligonucleotide modulates expression of an immune-related or immunomodulatory gene expressed by the T-cell by altering isoform expression of PD-1,
   wherein the antisense oligonucleotide is capable of inducing exon skipping by annealing to the pre-mRNA of the immune-related or immunomodulatory gene,
   and wherein the antisense oligonucleotide has either a maximum length of 30 nucleotides and comprises the sequence of SEQ ID NO: 6508 or consists of the sequence of SEQ ID NO: 69648.

2. The antisense oligonucleotide according to claim 1, wherein specific hybridization of the oligonucleotide to a target region of a PD-1 RNA in exon 2 switches membrane-bound PD-1 expression to soluble isoform PD-1 expression.

3. The antisense oligonucleotide according to claim 1, wherein the antisense oligonucleotide comprises a modified polynucleotide backbone.

4. The antisense oligonucleotide according to claim 3, wherein the modified polynucleotide backbone comprises at least one modified internucleotide linkage.

5. The antisense oligonucleotide according to claim 1, wherein the antisense oligonucleotide comprises a backbone which is selected from the group comprising of ribonucleic acid, deoxyribonucleic acid, DNA phosphorothioate, RNA phosphorothioate, 2'-O-methyl-oligoribonucleotide and 2'-O-methyl-oligodeoxyribonucleotide, 2'-O-hydrocarbyl ribonucleic acid, 2'-O-hydrocarbyl DNA, 2'-O-hydrocarbyl RNA phosphorothioate, 2'-O-hydrocarbyl DNA phosphorothioate, 2'-F-phosphorothioate, 2'-F-phosphodiester, 2'-methoxyethyl phosphorothioate, 2-methoxyethyl phosphodiester, deoxy methylene (methylimino) (deoxy MMI), 2'-O-hydrocarby MMI, deoxy-methylphos-phonate, 2'-O-hydrocarbyl methylphosphonate, morpholino, 4'-thio DNA, 4'-thio RNA, peptide nucleic acid, 3'-amidate, deoxy 3'-amidate, 2'-O-hydrocarbyl 3'-amidate, locked nucleic acid, cyclohexane nucleic acid, tricycle-DNA, 2'fluoro-arabino nucleic acid, N3'-P5' phosphoroamidate, carbamate linked, phosphotriester linked, a nylon backbone modification and mixtures of the aforementioned backbones.

6. The antisense oligonucleotide according to claim 1, wherein the oligonucleotide is chemically linked to one or more conjugates that enhance the activity, cellular distribution, or cellular uptake of the antisense oligonucleotide.

7. A method of treating a disease in a patient, the method comprising administering an antisense oligonucleotide according to claim 1, wherein the disease is cancer and/or a viral infection, or an autoimmune disease.

8. The method according to claim 7, wherein the antisense oligonucleotide has been transfected in a T cell, and the method comprising administering the transfected T cell to the patient.

9. An isolated T-cell transformed or transfected with an antisense oligonucleotide according to claim 1.

10. The antisense oligonucleotide according to claim 1, wherein the antisense oligonucleotide has a backbone comprising ribonucleic acid (RNA) or chemically modified RNA.

11. The antisense oligonucleotide according to claim 3, wherein the modified polynucleotide backbone comprises a modified sugar moiety.

12. The antisense oligonucleotide according to claim 11, wherein the modified moiety selected from the group consisting of phosphorodiamidate morpholino oligomer (PMO), peptide-conjugated phosphorodiamidate morpholino oligomer (PPMO), and non-peptide dendrimeric octaguanidine moiety-tagged morpholino oligomer.

13. The antisense oligonucleotide according to claim 4, wherein the modified internucleotide linkage comprises a modified phosphate.

14. The antisense oligonucleotide according to claim 13, wherein the modified phosphate is selected from the group comprising of a non-bridging oxygen atom substituting a sulfur atom, a phosphonate, a phosphorothioate, a phosphodiester, a phosphoromorpholidate, a phosphoropiperazidate and a phosphoroamidate.

15. The method according to claim 7, wherein the disease is cancer, and the patient is administered a further anti-cancer agent or treatment.

16. The method according to claim 8, wherein the antisense oligonucleotide is transfected or introduced to the T cell by any one selected from the group comprising: sonophoresis, electric pulsing, electroporation, osmotic shock, calcium phosphate precipitation, and DEAE dextran transfection, lipid mediated delivery, and passive delivery.

17. An antisense oligonucleotide having a maximum length of 30 nucleotides and comprising the sequence of SEQ ID NO: 6508.

18. An antisense oligonucleotide consisting of the sequence of SEQ ID NO: 69648, wherein the antisense oligonucleotide is a chemically modified RNA comprising at least one 2'-O-methoxyethyl modification.

19. The antisense oligonucleotide according to claim 17, wherein the antisense oligonucleotide is a chemically modified RNA comprising at least one 2'-O-methoxyethyl modification.

20. The antisense oligonucleotide according to claim 18, wherein the antisense oligonucleotide is a chemically modified RNA comprising a backbone comprising 2'-methoxyethyl phosphorothioate.

21. The antisense oligonucleotide according to claim 19, wherein the antisense oligonucleotide is a chemically modified RNA comprising a backbone comprising 2'-methoxyethyl phosphorothioate.

22. The method according to claim 7, wherein a pharmaceutical composition comprising the antisense oligonucleotide and a pharmaceutically acceptable carrier is administered, and wherein the carrier is selected from the group consisting of a nanoparticle, a liposome, a pH-sensitive liposome, an antibody conjugated liposome, a viral vector, a cationic lipid, a polymer, a UsnRNA, a U7 snRNA, and a cell penetrating peptide.

23. The method according to claim 22, wherein the administration is oral, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular.

24. The method according to claim 7, wherein the disease is a cancer selected from the group consisting of hepatitis B virus induced hepatocellular carcinoma and Epstein-Barr virus induced Non-Hodgkin Lymphoma.

* * * * *